(12) United States Patent
Okamoto et al.

(10) Patent No.: US 10,799,142 B2
(45) Date of Patent: Oct. 13, 2020

(54) PET-MRI APPARATUS AND RADIO FREQUENCY COIL

(71) Applicant: Toshiba Medical Systems Corporation, Otawara-shi (JP)

(72) Inventors: Kazuya Okamoto, Saitama (JP); Kazuto Nakabayashi, Kawasaki (JP)

(73) Assignee: CANON MEDICAL SYSTEMS CORPORATION, Otawara-shi (JP)

(*) Notice: Subject to any disclaimer, the term of this patent is extended or adjusted under 35 U.S.C. 154(b) by 385 days.

(21) Appl. No.: 15/651,269

(22) Filed: Jul. 17, 2017

(65) Prior Publication Data
US 2018/0028092 A1    Feb. 1, 2018

(30) Foreign Application Priority Data

Jul. 26, 2016   (JP) ................. 2016-146002

(51) Int. Cl.
| | |
|---|---|
| *A61B 5/055* | (2006.01) |
| *A61B 6/00* | (2006.01) |
| *A61B 5/00* | (2006.01) |
| *A61B 6/03* | (2006.01) |
| *G01R 33/385* | (2006.01) |
| *G01R 33/422* | (2006.01) |
| *G01R 33/34* | (2006.01) |
| *G01R 33/30* | (2006.01) |
| *G01R 33/48* | (2006.01) |

(52) U.S. Cl.
CPC .......... *A61B 5/055* (2013.01); *A61B 5/0035* (2013.01); *A61B 6/037* (2013.01); *A61B 6/4417* (2013.01);
(Continued)

(58) Field of Classification Search
CPC ....... A61B 5/055; A61B 5/0035; A61B 6/037; A61B 6/4417; G01R 33/385;
(Continued)

(56) References Cited

U.S. PATENT DOCUMENTS 8,131,340 B2 * 3/2012 Eberlein .......... G01R 33/34046
600/407
2007/0102641 A1   5/2007 Schmand et al.
(Continued)

FOREIGN PATENT DOCUMENTS

JP    2006-280929 A    10/2006
JP    2008-525161 A    7/2008
(Continued)

OTHER PUBLICATIONS

Japanese Office Action dated Apr. 14, 2020 in corresponding Japanese Patent Application No. 2016-146002, 4 pages.

*Primary Examiner* — Theodore J Stigell
*Assistant Examiner* — Sean A Frith
(74) *Attorney, Agent, or Firm* — Oblon, McClelland, Maier & Neustadt, L.L.P.

(57) ABSTRACT

A PET-MRI apparatus according to an embodiment includes a static magnetic field magnet, a gradient coil, a birdcage-type radio frequency coil, and at least one PET detector. The static magnetic field magnet is configured to generate a static magnetic field. The gradient coil is configured to apply a gradient magnetic field to a subject placed in the static magnetic field. The radio frequency coil includes two end rings and a plurality of rungs arranged at intervals along a circumferential direction of the end rings and is configured to transmit a radio frequency pulse or to receive a magnetic resonance signal from the subject. Further, the PET detector is housed inside a conductor structuring the rungs of the radio frequency coil.

13 Claims, 14 Drawing Sheets

(52) U.S. Cl.
CPC .......... *G01R 33/385* (2013.01); *G01R 33/307* (2013.01); *G01R 33/34076* (2013.01); *G01R 33/422* (2013.01); *G01R 33/481* (2013.01)

(58) Field of Classification Search
CPC ............ G01R 33/307; G01R 33/34076; G01R 33/422; G01R 33/481
See application file for complete search history.

(56) References Cited

U.S. PATENT DOCUMENTS

| | | | | |
|---|---|---|---|---|
| 2012/0169341 | A1* | 7/2012 | McKinnon | A61B 6/037 |
| | | | | 324/318 |
| 2013/0147480 | A1* | 6/2013 | Sueoka | A61B 5/055 |
| | | | | 324/309 |
| 2013/0211233 | A1* | 8/2013 | Yamaya | G01T 1/1603 |
| | | | | 600/411 |
| 2013/0284936 | A1* | 10/2013 | McBroom | G01R 33/481 |
| | | | | 250/363.03 |
| 2013/0296689 | A1* | 11/2013 | Okamoto | G01R 33/34046 |
| | | | | 600/411 |
| 2015/0369890 | A1 | 12/2015 | Schmand et al. | |
| 2017/0299675 | A1* | 10/2017 | Rigla Perez | G01T 1/202 |

FOREIGN PATENT DOCUMENTS

| | | | |
|---|---|---|---|
| JP | 2012-95819 | A | 5/2012 |
| JP | 2012-152551 | A | 8/2012 |
| WO | WO 2012/056504 | A1 | 5/2012 |

* cited by examiner

PET-MRI APPARATUS AND RADIO FREQUENCY COIL

CROSS-REFERENCE TO RELATED APPLICATIONS

This application is based upon and claims the benefit, of priority from Japanese Patent Application No. 2016-146002, filed on Jul. 26, 2016; the entire contents of which are incorporated herein by reference.

FIELD

Embodiments described herein relate generally to a PET-MRI apparatus and a radio frequency coil.

BACKGROUND

Conventionally, PET (Positron Emission Tomography)—CR (Computed Tomography) apparatuses in which a PET apparatus and an X-ray CT apparatus are combined together have been available as commercial products and have primarily been used in medical examinations for cancer and the like. On the other hand, for medical examination of the head of a subject, for example, Magnetic Resonance Imaging (MRI) apparatuses are primarily used, instead of x-ray CT apparatuses. Further, in recent years, it has been discussed to apply PET apparatuses to the head of a subject, and in particular, to use PET apparatuses in diagnosing Alzheimer's disease or the like. Thus, there is a demand for realizing a PET-MRI apparatus in which an MRI apparatus and a PET apparatus are combined together.

In this regard, because MRI apparatuses are configured to form a strong magnetic field, when an MRI apparatus is combined with a PET apparatus, it would be difficult to use photomultiplier tubes that are used in conventional PET apparatuses. For this reason, for example, as an apparatus in which an MRI apparatus is combined with a PET apparatus, a proposal has been made with an apparatus in which scintillators and silicon photomultipliers (SiPM) or photodiodes are incorporated in the bore of an MRI apparatus. Further, for example, another apparatus capable of performing MRI imaging and PET imaging at the same time has also been proposed in which PET detectors that are arranged in a ring formation are disposed in the bore of an MRI apparatus, while a transmitting/receiving coil used for imaging the head of a subject is installed on the inside thereof.

However, when the PET detectors are disposed in the bore of the MRI apparatus, there is a possibility that the image quality of MR images may be deteriorated by interference of the PET detectors with a radio frequency coil of the MRI apparatus.

DETAILED DESCRIPTION

A PET-MRI apparatus according to an embodiment includes a static magnetic field magnet, a gradient coil, a birdcage-type radio frequency coil, and at least one PET detector. The static magnetic field magnet is configured to generate a static magnetic field. The gradient coil is configured to apply a gradient magnetic field to a subject placed in the static magnetic field. The radio frequency coil includes two end rings and a plurality of rungs arranged at intervals along a circumferential direction of the end rings and is configured to transmit a radio frequency pulse or to receive a magnetic resonance signal from the subject. Further, the PET detector is housed inside a conductor structuring the rungs of the radio frequency coil.

Exemplary embodiments of a PET-MRI apparatus and a radio frequency coil will be explained in detail below, with reference to the accompanying drawings.

First Embodiment

Figure 1:
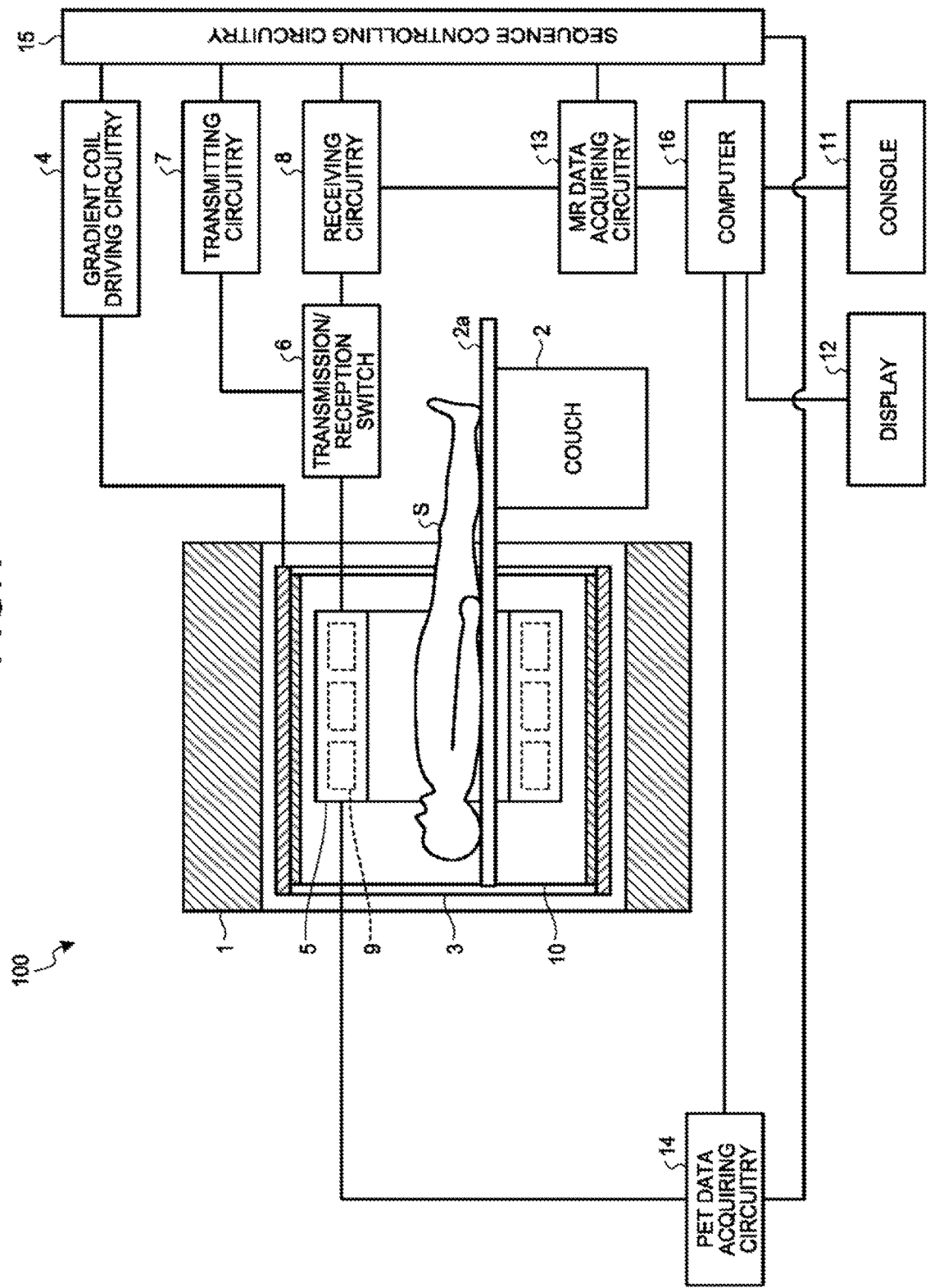
FIG. 1 is a diagram illustrating an exemplary configuration of a PET-MRI apparatus according to a first embodiment.

FIG. 1 is a diagram illustrating an exemplary configuration of a PET-MRI apparatus according to a first embodiment. For example, as illustrated in FIG. 1, a PET-MRI apparatus 100 according to the first embodiment, includes a static magnetic field magnet 1, a couch 2, a gradient coil 3, gradient coil driving circuitry 4, a transmitting and receiving radio frequency coil 5, a transmission/reception switch 6, transmitting circuitry 7, receiving circuitry 8, a plurality of PET detectors 9, a radio frequency shield 10 a console 11, a display 12, MR data acquiring circuitry 13, PET data acquiring circuitry 14, sequence controlling circuitry 15, and a computer 16. The static magnetic field magnet 1 and the gradient coil 3 are housed in a gantry.

The static magnetic field magnet 1 is formed to have a hollow and substantially circular cylindrical shape and is configured to generate a uniform static magnetic field in an imaging area (a bore) formed on the inner circumferential side thereof. For example, the static magnetic field magnet 1 may be realized with a permanent magnet, a superconductive magnet, or the like.

The couch 2 includes a couchtop 2a on which a subject 2 is placed. When an imaging data acquisition process is performed on the subject S, the couchtop 2a on which the subject S is placed is inserted into the imaging area formed on the inner circumferential side of the static magnetic field magnet 1 and the gradient coil 3.

The gradient coil 3 is formed to have a hollow and substantially circular cylindrical shape and is installed on the inner circumferential side of the static magnetic field magnet 1. Further, the gradient coil 3 includes three coils configured to generate, in the imaging area, gradient magnetic fields of which magnetic field strengths linearly change along X-, Y-, and Z-directions, respectively, that are orthogonal to one another. Further, when an imaging data acquisition process is performed on the subject S, the gradient coil 3 is configured to apply a gradient magnetic field to the subject S placed in the static magnetic field generated by the static magnetic field magnet 1.

The gradient coil driving circuitry 4 is configured to apply gradient magnetic fields Gx, Gy, and Gz to the imaging area, by individually supplying an electric current to the three coils included in the gradient coil 3.

The transmitting and receiving radio frequency coil 5 is a coil for the entire body of the subject (which may be called a "whole body coil") installed on the inside of the static magnetic field magnet 1 and the gradient coil 3. The transmitting and receiving radio frequency coil 5 is configured both to transmit a radio frequency magnetic field to the subject S and to receive a magnetic resonance signal emitted from the subject S.

More specifically, the transmitting and receiving radio frequency coil 5 is a whole body coil formed to have a hollow and substantially circular cylindrical shape and is installed on the inner circumferential side of the gradient coil 3. Further, when an imaging data acquisition process is performed on the subject S, the transmitting and receiving radio frequency coil 5 is configured to irradiate a radio frequency magnetic field to the subject S placed in the imaging area, on the basis of a radio frequency pulse output from the transmission/reception switch 6. Further, the transmitting and receiving radio frequency coil 5 is configured to detect the magnetic resonance signal emitted from the subject S as a result of the irradiation of the radio frequency magnetic field and to output the detected magnetic resonance signal to the transmission/reception switch 6.

During transmission and during reception (or not-transmission), the transmission/reception switch 6 is configured to switch between operations of the transmitting and receiving radio frequency coil 5. More specifically, at the time of transmission, the transmission/reception switch 6 outputs the radio frequency pulse output from the transmitting circuitry 7 to the transmitting and receiving radio frequency coil 5. At the time of reception (or not-transmission), the transmission/reception switch 6 outputs the magnetic resonance signal detected by the transmitting and receiving radio frequency coil 5 to the receiving circuitry 8.

The transmitting circuitry 7 is configured to output the radio frequency pulse to the transmitting and receiving radio frequency coil 5 via the transmission/reception switch 6. The receiving circuitry 8 is configured to receive the magnetic resonance signal from the transmitting and receiving radio frequency coil 5 via the transmission/reception switch 6 and to output the received magnetic resonance signal to the MR data acquiring circuitry 13.

The plurality of PET detector 9 are provided within the transmitting and receiving radio frequency coil 5 and are each configured to detect gamma rays (which means annihilation radiation) emitted from a positron emitting nuclide administered to the subject S. Further, each of the PET detectors 9 is configured to output count information based on the detected gamma rays to the PET data acquiring circuitry 11. For example, each of the PET detectors 9 includes signal detectors configured to detect the gamma rays and electronic devices such as an amplifier, an analog/digital (A/D) converter, and the like.

The radio frequency shield 10 is formed to have a hollow and substantially circular cylindrical shape and is positioned between the gradient coil 3 and the transmitting and receiving radio frequency coil 5. For example, the radio frequency shield 10 is a member having a circular cylindrical shape and being formed by using a copper foil, stainless steel mesh, or the like. The radio frequency shield 10 is configured to shield members positioned on the outside thereof such as the gradient coil 3 from the radio frequency magnetic field generated from the transmitting and receiving radio frequency coil 5, so as to prevent interference.

The console 11 is configured to receive input operations of various types of instructions and various types of information from an operator, to further convert the received input operations into electrical signals, and to output the electrical signals to the computer 16. For example, the console 11 may be realized by using a trackball, a switch button, a mouse, a keyboard, a touch panel, and/or the like.

The display 12 is configured to display various types of information and various types of images output from the computer 16. For example, the display 12 may be realized by using a liquid crystal monitor, a Cathode Ray Tube (CRT) monitor, a touch panel, or the like.

The MR date acquiring circuitry 13 is configured to generate Magnetic Resonance (MR) data by acquiring the magnetic resonance signal output, from the receiving circuitry 8, which amplifies and detects the acquired magnetic resonance signal, and subsequently performs an A/D conversion thereon. After that, the MR data acquiring circuitry 13 is configured to output the generated MR data to the computer 16.

The PET data acquiring circuitry 14 is configured to generate coincidence list information indicating one or more sets each made up of pieces of count information of gamma rays emitted from the positron emitting nuclide and detected substantially at the same time, by using the gamma ray count information sent thereto from the PET detectors 9. Further, the PET data acquiring circuitry 14 is configured to output the generated coincidence list information to the computer 16. Also, the PET data acquiring circuitry 14 is configured to output a control signal output from the sequence controlling circuitry 15 to the PET detectors 9.

The sequence controlling circuitry 15 is configured to execute various types of sequences by driving the gradient coil driving circuitry 4, the transmitting circuitry 7, the receiving circuitry 8, the MR data acquiring circuitry 13, and the PET data acquiring circuitry 14, on the basis of sequence execution data output from the computer 16. In this situation, the sequence execution data is information defining a procedure performed to acquire data used for generating an MR image or a PET image and is information defining timing with which the gradient coil driving circuitry 4, the transmitting circuitry 7, the receiving circuitry 8, the MR data acquiring circuitry 13, and the PET data acquiring circuitry 14 are driven.

The computer 16 is configured to control the entirety of the PET-MRI apparatus 100. For example, the computer 16 is configured to receive the various types of input operations from the operator via the console 11 and to control any of the constituent units of the PET-MRI apparatus 100 in response to the received operations. Further, the computer 16 is configured to output various types of information and various types of images to the display 12.

More specifically, the computer 16 includes a storage and controlling circuitry. The storage is configured to store therein various types of data. For example, the storage may foe realized by using a semiconductor memory element such as a Random Access Memory (RAM) or a flash memory, or a hard disk, an optical disk, or the like. The controlling circuitry has, for example, an data acquisition condition setting function, an MR image generating function, and a PET image generating function.

The data acquisition condition setting function is configured to receive an input of a data acquisition condition from the operator via the console 11 and to generate the sequence execution data for the purpose of acquiring the data used for generating the MR linage or the PET image on the basis of the input data acquisition condition. After that, by outputting the generated sequence execution data to the sequence controlling circuitry 15, the data acquisition condition setting function causes the sequence controlling circuitry 15 to execute any of various types of sequences.

The MR image generating function is configured to generate a two- or three-dimensional MR image on the basis of the MR data sent thereto from the MR data acquiring circuitry 13. Further, the MR image generating function is configured to cause the display 12 to display the generated MR Image in response to a request from the operator.

The PET image generating function is configured to generate a two- or three-dimensional PET image by using the coincidence list information generated by the PET data acquiring circuitry 14 as projection data. Further, the PET linage generating function is configured to cause the display 12 to display the generated PET image in response to a request from the operator.

In this situation, for example, processing circuitries such as the MR data acquiring circuitry 13, the PET data acquiring circuitry 14, the sequence controlling circuitry 15, and the controlling circuitry of the computer 16 are realized by using processors. In that situation, for example, processing functions of the processing circuitries are stored in the storage of the computer 16 in the form of computer-executable programs. Further, each of the processing circuitries realizes the processing function thereof corresponding to a different one of the programs, by reading the program from the storage and executing the read program.

Each of the processors mentioned above denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). It is also acceptable to directly incorporate the programs into the circuities of the processors, instead of storing the programs in the storage. In that situation, each of the processors realizes the functions thereof by reading and executing the program incorporated in the circuitry thereof. Further, as for the processors according to the first embodiment, each of the processors may be structured as a single circuit. Alternatively, it is also acceptable to realize the functions of the processors by structuring a single processor by combining together a plurality of independent circuits.

Further, although FIG. 1 illustrates the example in which the MR data acquiring circuitry 13, the PET data acquiring circuitry 14, the sequence controlling circuitry 15, and the controlling circuitry of the computer 16 are each realized as an independent processing circuitry, possible embodiments are not limited to this example. For instance, the processing functions of the processing circuitries may be realized as being distributed among a plurality of processing circuits or being integrated together into a single processing circuit, as appropriate.

Further, the PET-MRI apparatus 100 according to the first embodiment structured as described above is configured so that, as explained below, it is possible to reduce image quality deterioration that may be caused in the MR image by the PET detectors 9.

More specifically, in the first embodiment, the transmitting and receiving radio frequency coil 5 is a birdcage-type radio frequency coil arranged to enclose therein the subject S and includes two end rings and a plurality of rungs that are arranged at intervals along the circumferential direction of the end rings. Further, each of the rungs of the transmitting and receiving radio frequency coil 5 is configured to include at least one PET detector 9 and a radio frequency shield covering the periphery of said at least one PET detector 9.

Figure 2:
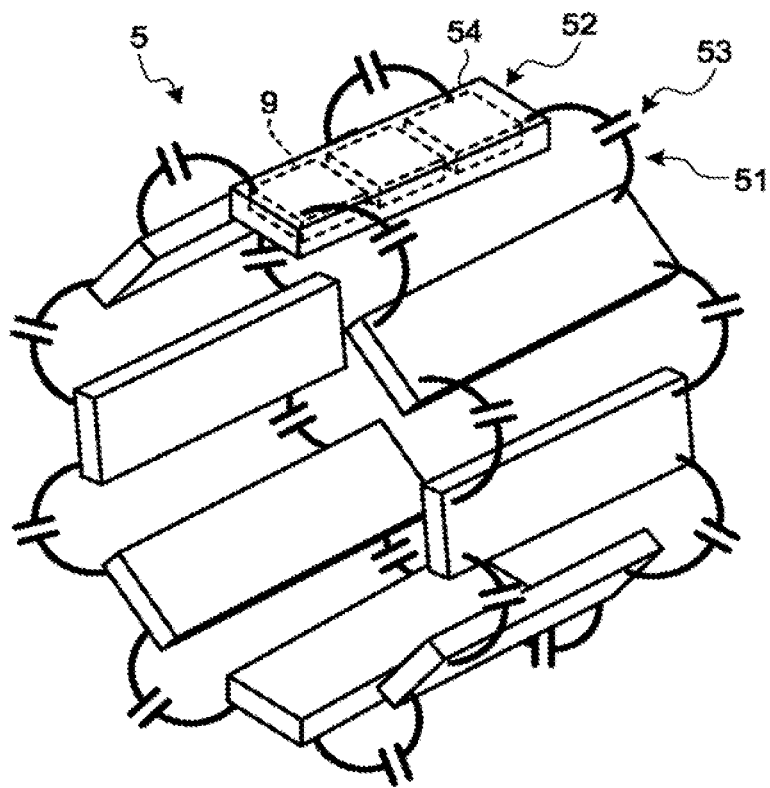
FIG. 2 is a drawing illustrating an exemplary configuration of a transmitting and receiving radio frequency coil according to the first embodiment.

FIG. 2 is a drawing illustrating an exemplary configuration of the transmitting and receiving radio frequency coil 5 according to the first embodiment. For example, as illustrated in FIG. 2, the transmitting and receiving radio frequency coil 5 is a birdcage-type radio frequency coil formed to have a substantially circular cylindrical shape and includes two end rings 51 and a plurality of rungs 52.

Each of the two end rings 51 is a coil conductor formed to have a ring shape. The two end rings 51 are disposed at either end of the transmitting and receiving radio frequency coil 5 in such a manner that the ring faces thereof oppose each other. Further, each of the plurality of rungs 52 is a coil conductor formed to have a bar shape. The plurality of rungs 52 are arranged at substantially regular intervals along the circumferential direction of the end rings 51. In this situation, each of the end rings 51 is structured by connecting together an end portion of each of the plurality of range 52, while interposing a capacitor 53 between any two adjacently-positioned rungs 52.

As explained above, the transmitting and receiving radio frequency coil 5 is regulated so as to generate a uniform radio frequency magnetic field at a desired frequency in the imaging area formed on the inner circumferential side thereof, by the rungs 52 arranged at the substantially regular intervals in the circumferential direction and the capacitors 53 interposed between the rungs 52. In other words, the transmitting and receiving radio frequency coil 5 is a so-called high-pass birdcage-type coil.

Further, for example, as illustrated in FIG. 2, each of the rungs 52 of the transmitting and receiving radio frequency coil 5 includes two or more PET detectors 9 arranged along the axial direction of the transmitting and receiving radio frequency coil 5, while an integrally-formed radio frequency shield 54 covers the periphery of the two or more PET detectors 9.

In other words, the PET detectors 9 are housed inside the conductors structuring the rungs 52 of the transmitting and receiving radio frequency coil 5. Further, the conductors structuring the rungs 52 each cover the periphery of two or more of the PET detectors 9 and function as the radio frequency shield 54.

With this arrangement, by covering the periphery of the PET detectors 5 with the radio frequency shields 54, it is possible to inhibit interference that may be caused on the transmitting and receiving radio frequency coil 5 by the PET detectors 9. The transmitting and receiving radio frequency coil 5 has sensitivity in the surroundings of the coil 5 including the inner imaging area. For this reason, for example, if the PET detectors 9 were disposed in the surroundings of the rungs 52, the transmitting and receiving radio frequency coil 5 might detect noise occurring from the electronic devices included in the PET detectors 9. In contrast, when the configuration described above is used, because the PET detectors 9 are arranged on the inside of the rungs 52, it is possible to inhibit the transmitting and receiving radio frequency coil 5 from detecting the noise occurring from the PET detectors 9. Accordingly, for example, by using the radio frequency shields 54, it is possible to inhibit the unwanted noise occurring from the electronic devices included in the PET detectors 9 from entering a reception signal of the magnetic resonance signal and to inhibit the efficiency of the transmitting and receiving-radio frequency coil 5 from being degraded by the PET detectors 9. As a result, it is possible to reduce image quality deterioration that may be caused in the MR image by the PET detectors 9. Further, it is also possible to keep small the impact made on the PET detectors 9 by the radio frequency magnetic field generated by the transmitting and receiving radio frequency coil 5.

Further, disposing the PET detectors 9 in the rungs 52 of the transmitting and receiving radio frequency coil 5 makes if possible to arrange the PET detectors 9 in the surroundings of a magnetic field center, which yields the highest image quality in MR images. As a result, for example, when an MR image and a PET image are taken of mutually the same region, it is possible to acquire both types of images in an excellent manner without the need to move the subject S.

In the above description, the example is explained in which, with respect to each of the rungs 52, the integrally-formed radio frequency shield 54 covers the periphery of the two or more PET detectors 9. However, possible configurations of the rungs are not limited to this example. For instance, another arrangement is also acceptable in which, with respect to each of the rungs including two or more PET detectors 9, one or more separate radio frequency shields each individually cover the periphery of one PET detector 9 or multiple PET detectors 9.

Figure 3:
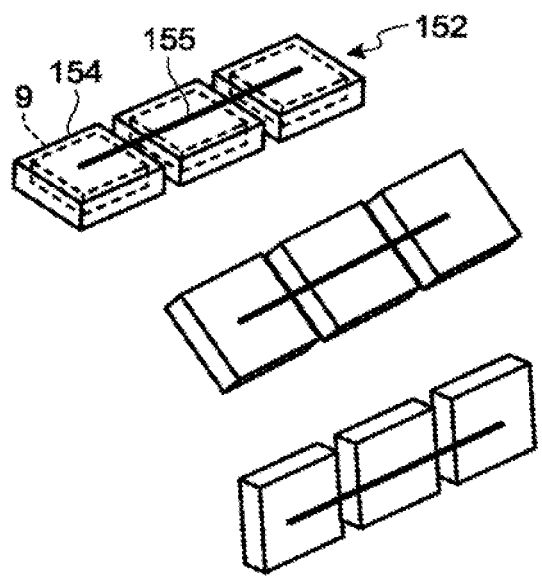
FIG. 3 is a drawing illustrating another exemplary configuration of a transmitting and receiving radio frequency coil according to the first embodiment.

FIG. 3 is a drawing illustrating another exemplary configuration of the transmitting and receiving radio frequency coil 5 according to the first embodiment. The example in FIG. 3 illustrates only a number of rungs among the rungs included in the transmitting and receiving radio frequency coil 5, for the sake of convenience in illustration. For example, as illustrated in FIG. 3, each of the rungs 152 includes two or more PET detectors 9 arranged along the axial direction of the transmitting and receiving radio frequency coil 5. Further, a separate radio frequency shield 154 individually covers the periphery of each of the plurality of PET detectors 9, while the radio frequency shields 154 are electrically connected to one another by conductor pieces 155, for example.

By providing the separate radio frequency shield individually for each of the PET detectors 9 in this manner, it is possible to form gaps in each rung. Because the radio frequency magnetic field is generated in the spaces formed between the coil conductors, forming the gaps in the rungs in this manner makes it possible to generate the radio frequency magnetic field more efficiently. As additional information, although FIG. 3 illustrates the example in which the separate radio frequency shield is individually provided for each of the PET detectors 9, one radio frequency shield may be provided for the two or more PET detectors 9 arranged along the axial direction.

Further, although FIGS. 2 and 3 illustrate the example in which each of the rungs includes three PET detectors 9 for the sake of convenience in illustration, the quantity of the PET detectors included in each of the rungs does not necessarily have to be three. For instance, the quantity of the PET detectors included in each of the rungs may be determined as appropriate in accordance with a specification required of the PET-MRI apparatus 100. In other words, each of the rungs is configured so as to include one PET detector 9 or two or more PET detectors 9 in accordance with the specification of the PET-MRI apparatus 100. In this situation, the larger the quantity of the PET detectors is, the larger is the area from which the gamma rays are detected, and also the larger is the area of which it is possible to take a PET image.

Figure 4:
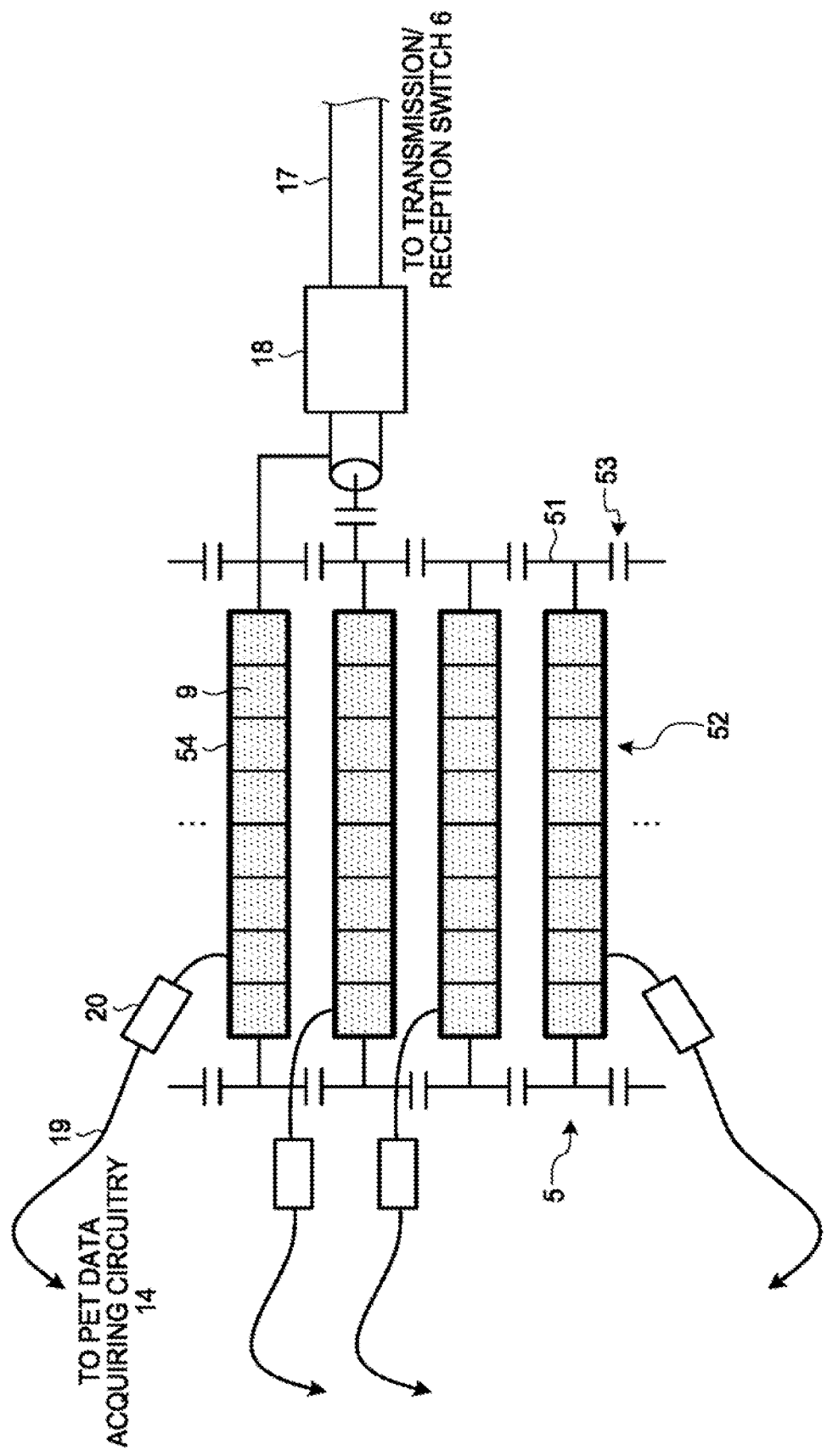
FIG. 4 is a drawing illustrating an example of an electrical connection of a radio frequency coil according to the first embodiment.

FIG. 4 is a drawing illustrating an example of an electrical connection of the transmitting and receiving radio frequency coil 5 according to the first embodiment. For example, as illustrated in FIG. 4, the PET-MRI apparatus 100 according to the first embodiment includes, as units being connected to the transmitting and receiving radio frequency coil 5, a transmitting and receiving cable 17, a radio frequency blocking circuitry 18, signal and control lines 19, and radio frequency blocking circuitries 20. Although the example in FIG. 4 illustrates each set of the signal and control lines 19 as a single line collectively for the sake of convenience in illustration, each of the signal and control lines 19 may be realized with a single line or multiple lines.

One end of the transmitting and receiving cable 17 is connected to the capacitors 53 interposed between the rungs 52, while the other end thereof is connected to the transmission/reception switch 6. Further, the transmitting and receiving cable 17 is configured to transfer the radio frequency pulse output from the transmission/reception switch 6 to the transmitting and receiving radio frequency coil 5 and to transfer the magnetic resonance signal output from the transmitting and receiving radio frequency coil 5 to the transmission/reception switch 6. In this situation, for example, the radio frequency blocking circuitry 18 is connected to the transmitting and receiving cable 17. The radio frequency blocking circuitry 18 is configured to block a radio frequency current flowing in outer coating of the transmitting and receiving cable 17.

One end of the signal and control lines 19 is connected to the PET detectors 9, while the other end thereof is connected to the PET data acquiring circuitry 14. In this situation, of the signal and control lines 19, the signal line is configured to transfer a control signal output from the PET data acquiring circuitry 14 to predetermined PET detectors 9, whereas the control line is configured to transfer the signal of the count information output from the predetermined PET detectors 9 to the PET data acquiring circuitry 14. Further, the signal and control lines 19 are shielded for the purpose of avoiding interference with the transmitting and receiving radio frequency coil 5 and further have a corresponding one of the radio frequency blocking circuitries 20 connected thereto. The radio frequency blocking circuitries 20 are also configured to block a radio frequency current flowing in outer coating of the signal and control lines 19.

Figure 5:
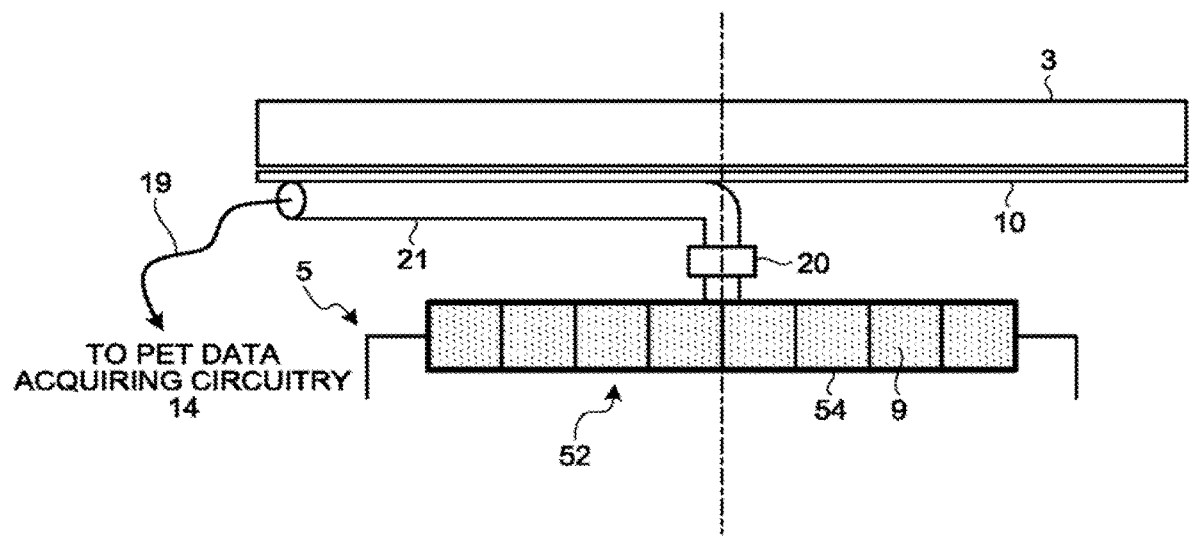
FIG. 5 is a drawing illustrating an exemplary configuration of signal and control lines connected to PET detectors according to the first embodiment.
Figure 6:
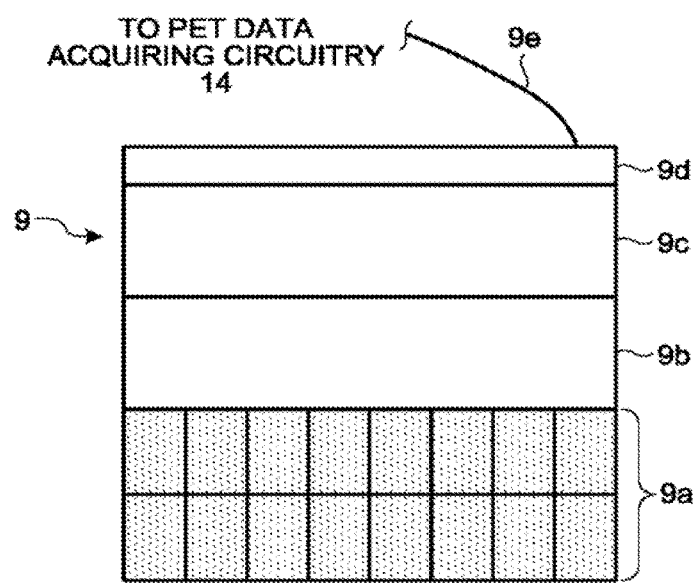
FIG. 6 is a drawing illustrating an exemplary configuration of any of the PET detectors according to the first embodiment.

FIG. 6 is a drawing illustrating an exemplary configuration of the signal and control lines connected to the PET detectors 9 according to the first embodiment. For example, as illustrated in FIG. 5, the signal and control lines 19 are bundled together and covered by a radio frequency shield 21. Further, for example, while being positioned on the inner circumferential side of the radio frequency shield 10 provided between the gradient coil 3 and the transmitting and receiving radio frequency coil 5, the radio frequency shield 21 are disposed so as to be in contact with the radio frequency shield 10.

By arranging the radio frequency shield 21, which covers the signal and control lines 13, so as to be in contact with the other radio frequency shield 10, it is possible to keep small the impact made on the transmitting and receiving radio frequency coil 5 by noise occurring on the paths of the signal and control lines 19.

Further, for example, the signal and control lines 19 covered by the radio frequency shield 21 are provided so as to extend on an equipotential surface (a ground) of the transmitting and receiving radio frequency coil 5.

By providing the signal and control lines 19 covered by the radio frequency shield 21 so as to extend on the equipotential surface of the transmitting and receiving radio frequency coil 5, it is possible to minimize a decrease in the efficiency of the transmitting and receiving radio frequency coil 5. Further, when the signal and control lines 19 covered by the radio frequency shield 21 are provided to extend along the equipotential surface with a high level of precision, it is not necessary to provide the radio frequency blocking circuitry 20.

By using this configuration, it is possible to absolutely keep small, the impact made on the transmitting and receiving radio frequency coil 5 by the PET detectors 9. Although the example is explained above in which both the signal line and the control line (of the signal and control lines 19) have the abovementioned configuration, it is also acceptable to configure one selected from between the signal line and the control line to have the abovementioned configuration.

FIG. 6 is a drawing illustrating an exemplary configuration of any of the PET detectors 9 according to the first embodiment. For example, as illustrated in FIG. 6, the PET detector 9 includes signal detectors 9a, an amplifier 3b, an A/B converter 3c, an input/output (I/O) interface 3d, and an optical fiber 3e.

Each of the signal detectors 9a is configured to detect a gamma ray by converting the gamma ray into an analog signal with the use of a semiconductor element. The amplifier 9b is configured to amplify the analog signals output from the signal detectors 9a. The A/D converter 9c is configured to convert the analog signals amplified by the amplifier 9b into digital signals. The I/O interface 9d is configured to convert the digital signals obtained by the A/D converter into optical signals. One end of the optical fiber 9e is connected to the I/O interface 9d, whereas the other end thereof is connected to the signal line extending to the PET data acquiring circuitry 14, so that the optical signals output from the I/O interface 9d are transferred to the PET data acquiring circuitry 14.

Further, as explained above, the PET detector 9 is covered by the radio frequency shield 54. Accordingly, it is possible to inhibit noise occurring from the A/D converter 9c or the like included in the PET detector 9 from traveling to the outside of the PET detector 9. Further, because the electrical signals detected by the signal detectors 9a are converted into the optical signals and transferred via the optical fiber 9e, it is possible to prevent noise from occurring on the transfer path. As a result, it is possible to further reduce the interference of the PET detectors 9 with the transmitting and receiving radio frequency coil 5.

As explained above, according to the first embodiment, it is possible to inhibit the interference of the PET detectors 9 with the transmitting and receiving radio frequency coil 5. It is therefore possible to reduce image quality deterioration that may be caused in the MR image by the PET detectors 9.

The first embodiment has thus been explained. It is also possible to carry out the first embodiment described above, while modifying a number of the constituent units as appropriate. In the following sections, modification examples of the first embodiment will be explained as other embodiments. In the explanations below, PET-MRI apparatuses according to various embodiments will be explained while focus is placed on differences from the first embodiment. Detailed explanations of some of the features that are the same as those in the first embodiment or in any other embodiment will be omitted. Also, in the explanations below and the drawings, some of the constituent units having the same functions will be referred to by using the same reference characters.

Second Embodiment

First, a second embodiment will be explained. The second embodiment corresponds to an example in which a radio frequency coil including the PET detectors 9 is a whole body coil installed on the inside of the static magnetic field magnet 1 and the gradient coil 3, while the radio frequency coil is configured to transmit a radio frequency magnetic field to the subject S.

Figure 7:
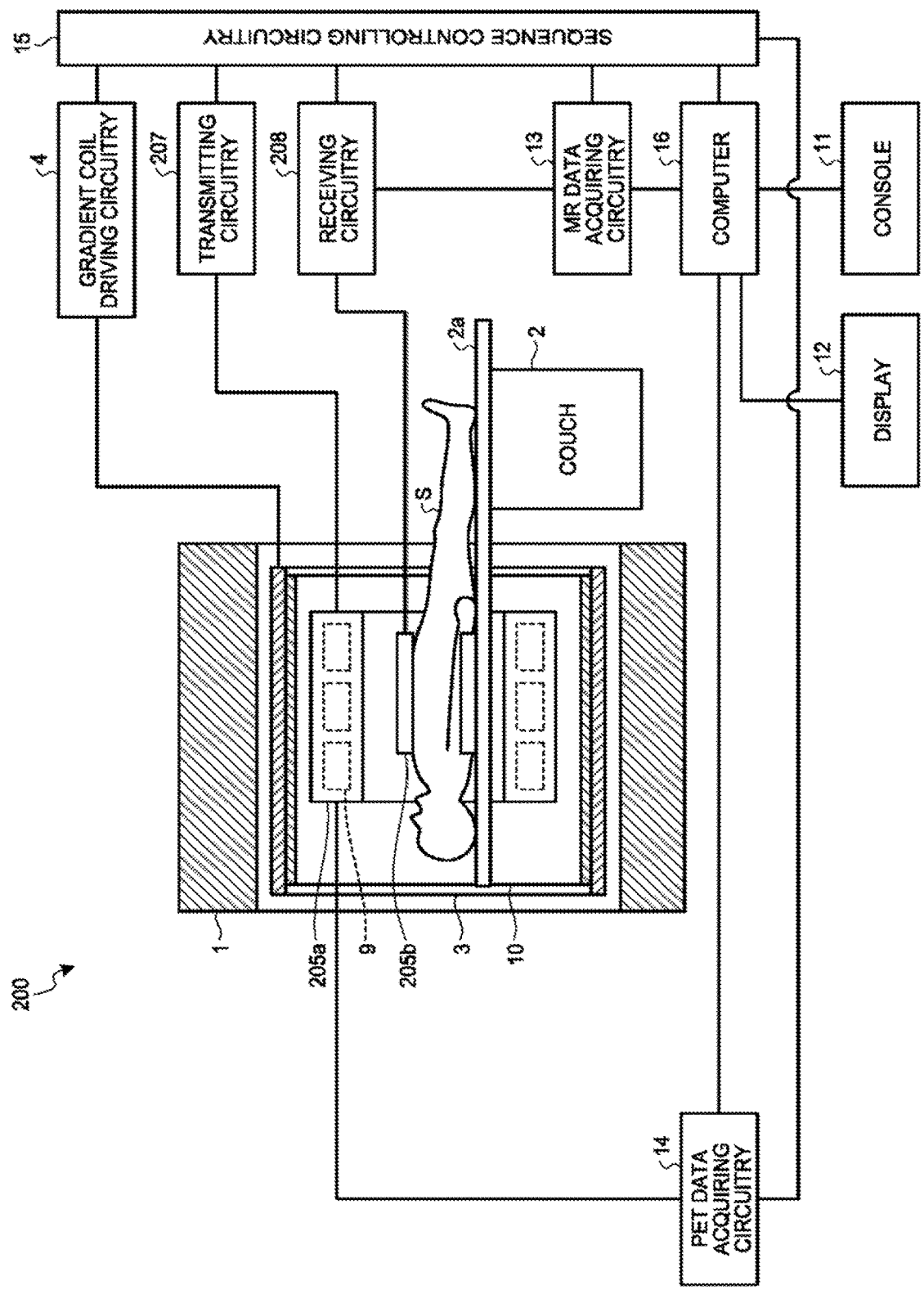
FIG. 7 is a diagram illustrating an exemplary configuration of a PET-MRI apparatus according to a second embodiment.

FIG. 7 is a diagram illustrating an exemplary configuration of a PET-MRI apparatus according to the second embodiment. For example, as illustrated in FIG. 7, a PET-MRI apparatus 200 according to the second embodiment includes the static magnetic field magnet 1, the couch 2, the gradient coil 3, the gradient coil driving circuitry 4, a transmitting radio frequency coil 200a, a receiving radio frequency coil 205b, transmitting circuitry 207, receiving circuitry 208, the plurality of PET detectors 9, the radio frequency shield 10, the console 11, the display 12, the MR data acquiring circuitry 13, the PET data acquiring circuitry 14, the sequence controlling circuitry 15, and the computer 16.

The transmitting radio frequency coil 205a is a whole body coil formed to have a hollow and substantially circular cylindrical shape and is installed on the inner circumferential side of and the gradient coil 3. Further, when an imaging data acquisition process is performed on the subject S, the transmitting radio frequency coil 205a is configured to irradiate a radio frequency magnetic field to the subject S placed in the imaging area, on the basis of the radio frequency pulse output from the transmitting circuitry 207.

The receiving radio frequency coil 205b is a local coil formed to have a hollow and substantially circular cylindrical shape and is provided on the couchtop 2a of the couch 2. Further, when an imaging data acquisition process is performed on the subject 2, the receiving radio frequency coil 205b is moved into the imaging area together with the couchtop 2a and is configured to detect a magnetic resonance signal emitted from the subject 5 as a result of the irradiation of the radio frequency magnetic field and to output the detected magnetic resonance signal to the receiving circuitry 208.

For example, the receiving radio frequency coil 205b may be a coil for the head, a coil for the neck, a coil for a shoulder, a coil for the chest, a coil for the abdomen, a coil for a leg, a coil for the spine, or the like. FIG. 7 illustrates an example in which the receiving radio frequency coil 205b is a coil for the abdomen.

The transmitting circuitry 207 is configured to output the radio frequency pulse to the transmitting radio frequency coil 205a. The receiving circuitry 208 is configured to receive the magnetic resonance signal from the receiving radio frequency coil 205b and to output the received magnetic resonance signal to the MR data acquiring circuitry 13.

With the configuration described above, in the second embodiment, the transmitting radio frequency coil 205a is a birdcage-type radio frequency coil arranged to enclose therein the subject S and includes two end rings and a plurality of rungs arranged at intervals along the circumferential direction of the end rings. Further, each of the rungs of the transmitting radio frequency coil 205a is configured to include at least one PET detector 9 and the radio frequency shield that covers the periphery of said at least one PET detector 2.

In this situation, the transmitting radio frequency coil 205a according to the second embodiment has a similar configuration to that of the transmitting and receiving radio frequency coil 5 explained in the first embodiment, except for the configuration for the reception. Accordingly, by using the transmitting radio frequency coil 205a according to the second embodiment, it is possible to inhibit the interference of the PET detectors 9 with the transmitting radio frequency coil 205a, similarly to the first embodiment.

Figure 8:
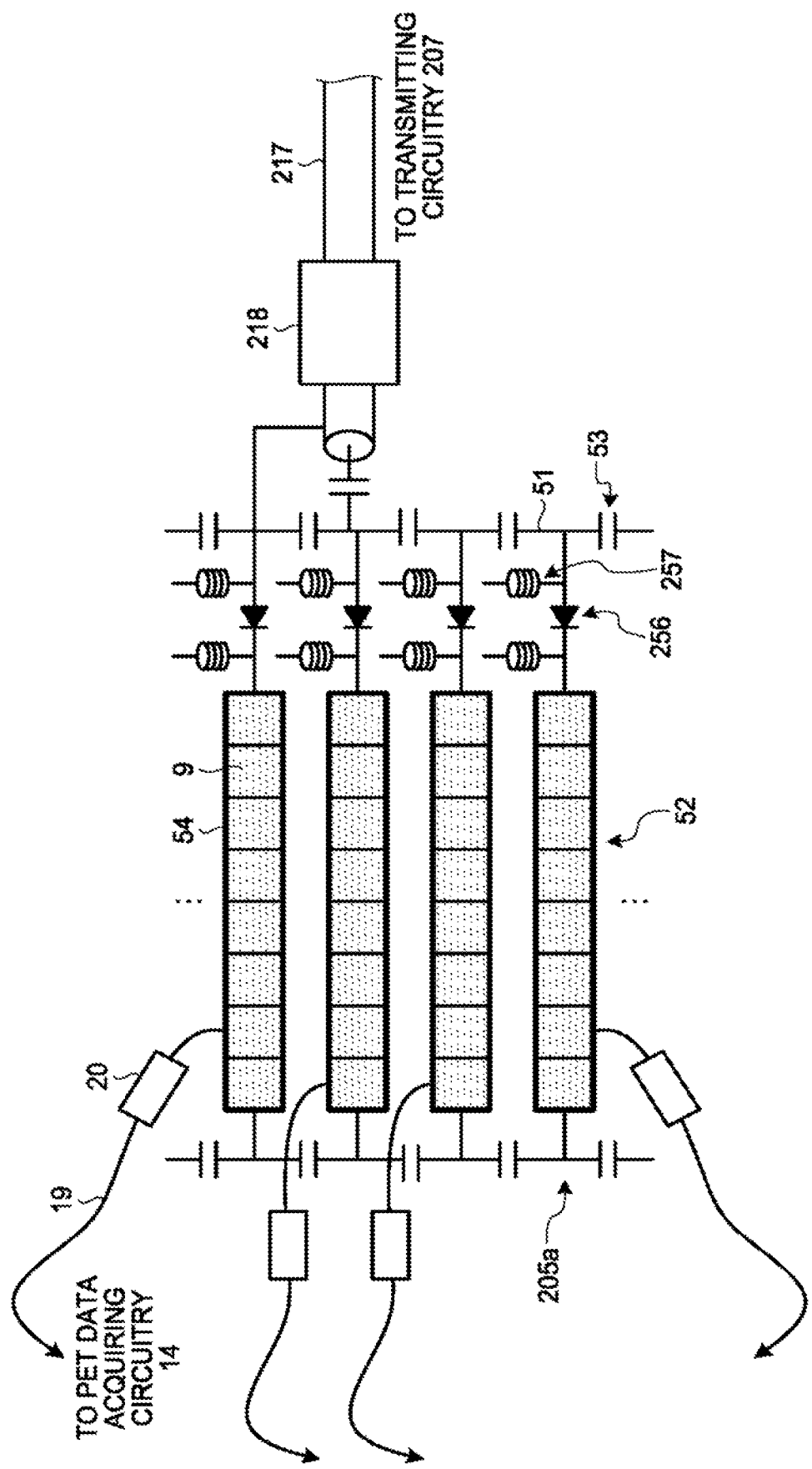
FIG. 8 is a drawing illustrating an example of an electrical connection of a transmitting radio frequency coil according to the second embodiment.

FIG. 8 is a drawing illustrating an example of an electrical connection of the transmitting radio frequency coil 205a according to the second embodiment. For example, as illustrated in FIG. 8, the PET-MRI apparatus 200 according to the second embodiment includes, as units being connected to the transmitting radio frequency coil 205a, a transmitting cable 217 extending to the transmitting circuitry 207, a radio frequency blocking circuitry 218 connected to the transmitting cable 217, the signal and control lines 19, and the radio frequency blocking circuitries 20.

Further, the transmitting radio frequency coil 205a further has a switching function that, for each of the rungs 52, brings the transmitting radio frequency coil 205a into a desired tuned state at the time of transmission and brings the transmitting radio frequency coil 205a into an untuned state at the time of reception.

For example, the transmitting radio frequency coil 205a has, as the switching function, PIN diodes 256 each of which is connected in series to a different one of the rungs 52 and two choke power supply cables 257 that are connected to the two ends of each of the PIN diodes 256 and are configured to supply electric power to the PIN diode 256.

At the time of transmission, the PIN diodes 256 are turned on as a result of an electric current flowing in the normal direction of the PIN diodes 256. As a result, the transmitting radio frequency coil 205a goes into the tuned state. In contrast, at the time of reception, the PIN diodes 256 are turned off as a result of a reverse voltage being applied to the PIN diodes 256 through the choke power supply cables 257. Accordingly, the transmitting radio frequency coil 205a goes into the untuned state, so that the receiving radio frequency coil 205b is able to receive the magnetic resonance signal.

As explained above, according to the second embodiment, similarly to the first embodiment, it is possible to inhibit the interference of the PET detectors 9 with the transmitting radio frequency coil 205a. It is therefore possible to reduce image quality deterioration that may be caused in the MR image by the PET detectors 9.

Third Embodiment

Next, a third embodiment will be explained. The third embodiment corresponds to an example in which a radio frequency coil including the PET detectors 9 is a local coil formed in accordance with an localized region of interest of the subject S and is configured both to transmit a radio frequency magnetic field to the subject S and to receive a magnetic resonance signal emitted from the subject S.

Figure 9:
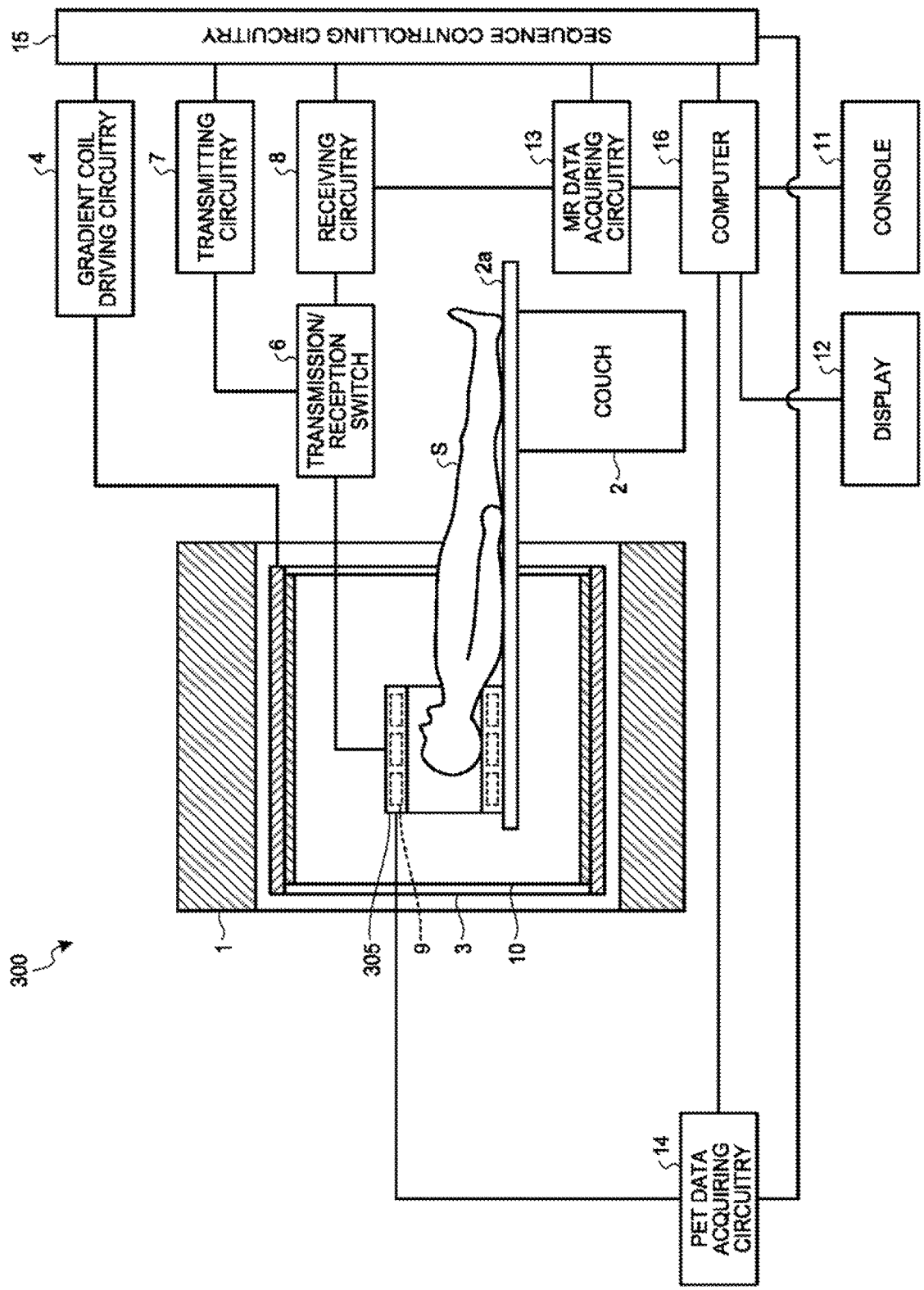
FIG. 9 is a diagram illustrating an exemplary configuration of a PET-MRI apparatus according to a third embodiment.

FIG. 9 is a diagram illustrating an exemplary configuration of a PET-MRI apparatus according to the third embodiment. For example, as illustrated in FIG. 9, a PET-MRI apparatus 300 according to the third embodiment, includes the static magnetic field magnet 1, the couch 2, the gradient coil 3, the gradient coil driving circuitry 4, a transmitting and receiving radio frequency coil 305, the transmission/reception switch 6, the transmitting circuitry 1, the receiving circuitry 8, the plurality of PET detectors 9, the radio frequency shield 10, the console 11, the display 12, the MR data acquiring circuitry 13, the PET data acquiring circuitry 14, the sequence controlling circuitry 15, and the computer 16.

The transmitting and receiving radio frequency coil 305 is a local coil formed to have a hollow and substantially circular cylindrical shape and is provided on the couchtop 2a of the couch 2. Further, when an imaging data acquisition process is performed on the subject S, the transmitting and receiving radio frequency coil 305 is moved into the imaging area together with the couchtop 2a and is configured to irradiate the radio frequency magnetic field to the subject S placed in the imaging area, on the basis of the radio frequency pulse output from the transmission/reception switch 6. Further, the transmitting and receiving radio frequency coil 305 is configured to detect the magnetic resonance signal emitted from the subject S as a result of the irradiation of the radio frequency magnetic field and to output the detected magnetic resonance signal to the transmission/reception switch 6.

For example, the transmitting and receiving radio frequency coil 305 may be a coil for the head, a coil for the neck, a coil for a shoulder, a coil for the chest, a coil for the abdomen, a coil for a leg, a coil for the spine, or the like. FIG. 9 illustrates an example in which the transmitting and receiving radio frequency coil 305 is a coil for the head.

With the configuration described above, in the third embodiment, the transmitting and receiving radio frequency coil 305 is a birdcage-type radio frequency coil arranged to enclose therein the subject S and includes two end rings and a plurality of rungs arranged at intervals along the circumferential direction of the end rings. Further, each of the rungs of the transmitting and receiving radio frequency coil 305 is configured to include at least one PET detector 9 and the radio frequency shield that covers the periphery of said at least one PET detector 9.

In this situation, the transmitting and receiving radio frequency coil 505 according to the third embodiment has a similar configuration to that of the transmitting and receiving radio frequency coil 5 explained in the first embodiment, although the size of the entirety thereof is smaller. Consequently, by using the transmitting and receiving radio frequency coil 305 according to the third embodiment, it is possible to inhibit the interference of the PET detectors 9 with the transmitting and receiving radio frequency coil 305, similarly to the first embodiment.

As explained above, according to the third embodiment, similarly to the first embodiment, it is possible to inhibit the interference of the PET detectors 9 with the transmitting and receiving radio frequency coil 305. It is therefore possible to reduce image quality deterioration that may be caused in the MR image by the PET detectors 9.

Fourth Embodiment

Next, a fourth embodiment will be explained. The fourth embodiment corresponds to an example in which a radio frequency coil, including the PET detectors 9 is a local coil formed in accordance with an localized region of interest of the subject S and is configured both to transmit a radio frequency magnetic field to the subject S and to receive a magnetic resonance signal emitted from the subject S. Further, the fourth embodiment corresponds to the example in which the radio frequency coil is arranged on a drivable table that is different from the couch 2.

Figure 10:
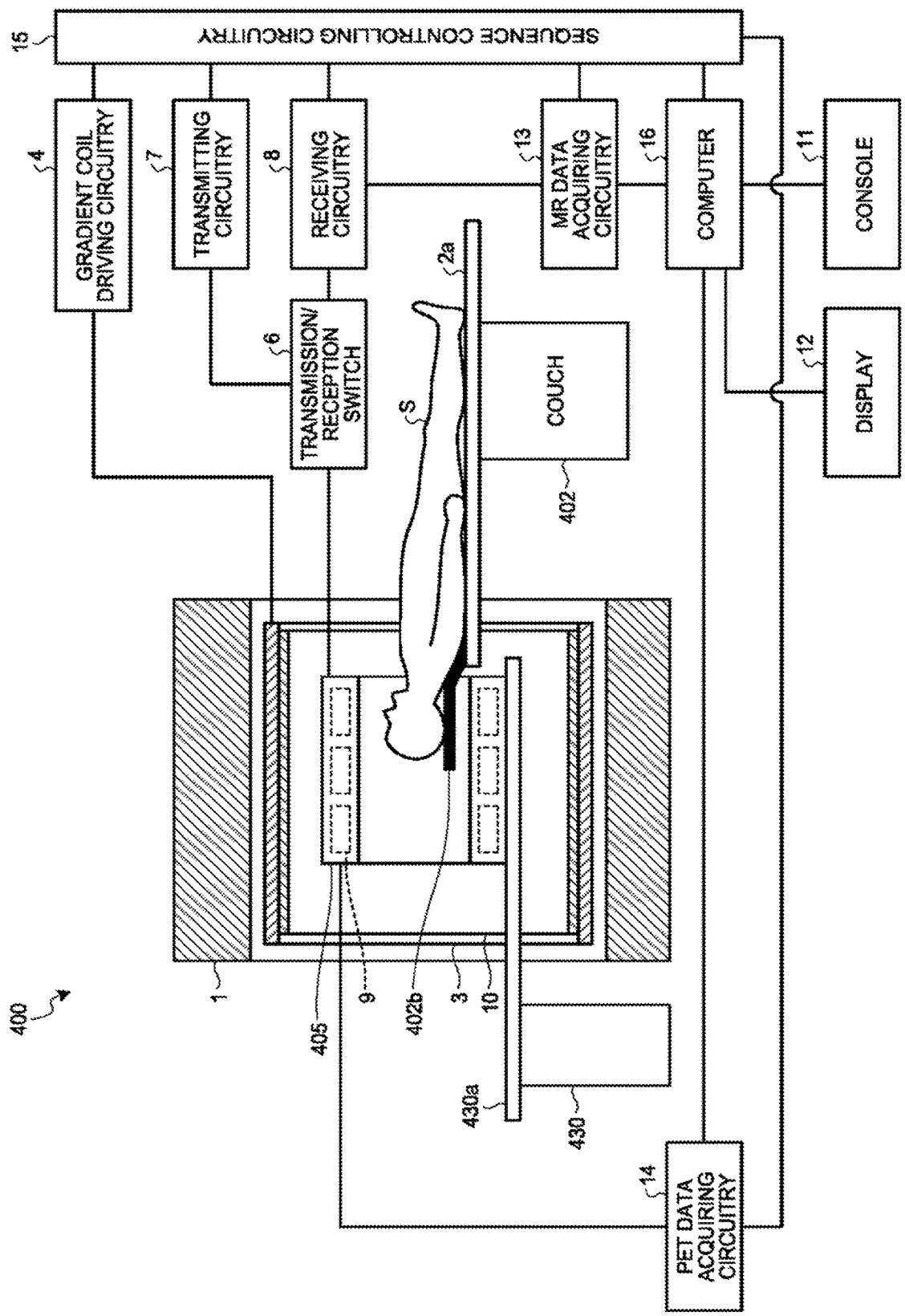
FIG. 10 is a diagram illustrating an exemplary configuration of a PET-MRI apparatus according to a fourth embodiment.

FIG. 10 is a diagram illustrating an exemplary configuration of a PET-MRI apparatus according to the fourth embodiment. For example, as illustrated in FIG. 10, a PET-MRI apparatus 400 according to the fourth embodiment includes the static magnetic field magnet 1, a couch 402, the gradient coil 3, the gradient coil driving circuitry 4, a transmitting and receiving radio frequency coil 405, the transmission/reception switch 6, the transmitting circuitry 3, the receiving circuitry 8, the plurality of PET detectors 9, the radio frequency shield 10, the console 11, the display 12, the MR data acquiring circuitry 13, the PET data acquiring circuitry 14, the sequence controlling circuitry 15, the computer 16, and a radio frequency coil insertion table 430.

The couch 402 includes the couchtop 2a on which the subject S is placed. When an imaging data acquisition process is performed on the subject S, the couchtop 2a on which the subject S is placed is moved into the imaging area formed on the inner circumferential side of the static magnetic field magnet 1 and the gradient coil 3.

Further, in the fourth embodiment, the couch 402 further includes a supporting member 402b attached to an end of the couchtop 2a positioned on the static magnetic field magnet 1 side. The supporting member 402b is provided so as to extend from the end of the couchtop 2a in the longitudinal direction of the couchtop 2a. When the subject S is placed on the couchtop 2a, a localized region of interest of the subject S is arranged on the supporting member 402b. Further, the supporting member 402b is formed to have such a dimension that allows the supporting member 402b to be inserted, together with the localized region of interest, on the inner circumferential side of the transmitting and receiving radio frequency coil 405. FIG. 10 illustrates an example in which the localized region of interest is the head.

The radio frequency coil insertion table 430 includes an insertion plate 430a with which the transmitting and receiving radio frequency coil 405 is arranged. When an imaging data acquisition process is performed on the subject S, the insertion plate 430a arranged with the transmitting and receiving radio frequency coil 405 is moved into the imaging area formed on the inner circumferential side of the static magnetic field magnet 1 and the gradient coil 3. In this situation, the radio frequency coil insertion table 430 is positioned on the side opposite from the couch 402 with respect to the static magnetic field magnet 1, so that the transmitting and receiving radio frequency coil 405 is moved into the imaging area from the side opposite to the side from which the subject S is moved into the imaging area. In this situation, the radio frequency coil insertion table 430 moves the transmitting and receiving radio frequency coil 405, in such a manner that the localized region of interest is positioned on the inner circumferential side of the transmitting and receiving radio frequency coil 105.

The transmitting and receiving radio frequency coil 405 is a local coil formed to have a hollow and substantially circular cylindrical shape and is provided on the insertion plate 430a of the radio frequency coil insertion table 430. Further, when an imaging data acquisition process is performed on the subject S, the transmitting and receiving radio frequency coil 405 is moved into the imaging area together with the insertion plate 430a and is configured to irradiate a radio frequency magnetic field to the subject S placed in the imaging area, on the basis of the radio frequency pulse output from the transmission/reception switch 6. Further, the transmitting and receiving radio frequency coil 405 is configured to detect the magnetic resonance signal emitted from the subject S as a result of the irradiation of the radio frequency magnetic field and to output the detected magnetic resonance signal to the transmission/reception switch 6.

For example, the transmitting and receiving radio frequency coil 405 may be a coil for the head, a coil for the neck, a coil for a leg, or the like. FIG. 10 illustrates an example in which the transmitting and receiving radio frequency coil 405 is a coil for the head.

With the configuration described above, in the fourth embodiment, the transmitting and receiving radio frequency coil 403 is a birdcage-type radio frequency coil arranged to enclose therein the subject S and includes two end rings and a plurality of rungs arranged at intervals along the circumferential direction of the end rings. Further, each of the rungs of the transmitting and receiving radio frequency coil 405 is configured to include at least one PET detector 9 and the radio frequency shield that covers the periphery of said at least one PET detector 9.

In this situation, the transmitting and receiving radio frequency coil 405 according to the fourth embodiment has a similar configuration to that of the transmitting and receiving radio frequency coil 5 explained in the first embodiment, although the size of the entirety thereof is smaller. Consequently, by using the transmitting and receiving radio frequency coil 405 according to the fourth embodiment, it is possible to inhibit the interference of the PET detectors 9 with the transmitting and receiving radio frequency coil 405, similarly to the first embodiment.

As explained above, according to the fourth embodiment, similarly to the first embodiment, it is possible to inhibit the interference of the PET detectors 9 with the transmitting and receiving radio frequency coil 405. It is therefore possible to reduce image quality deterioration that may be caused in the MR image by the PET detectors 9.

Fifth Embodiment

Next, a fifth embodiment will be explained. The fifth embodiment corresponds to an example in which a radio frequency coil including the PET detectors 9 is a local coil formed in accordance with a localized region of interest of the subject S and is configured to receive a magnetic resonance signal emitted from the subject S.

Figure 11:
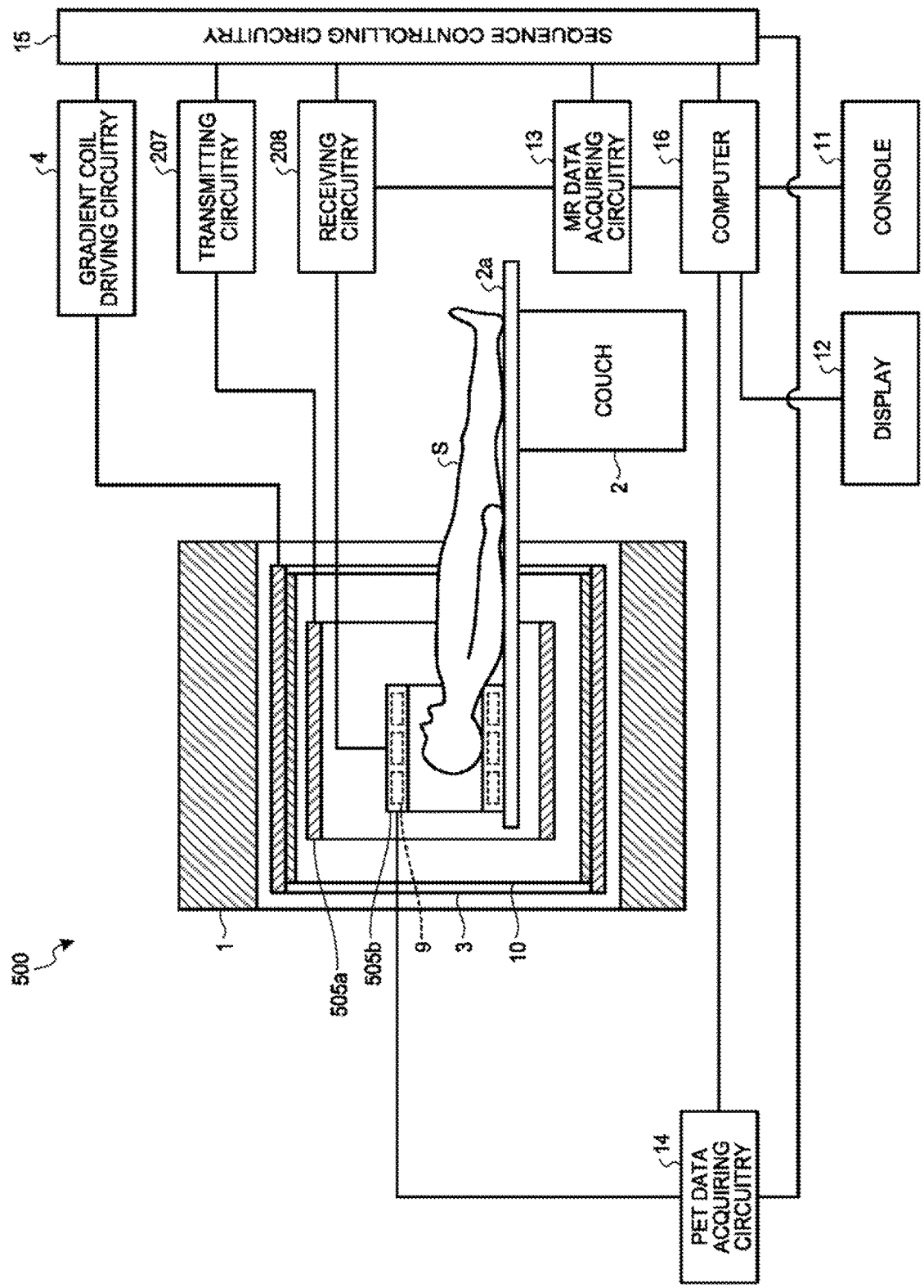
FIG. 11 is a diagram illustrating an exemplary configuration of a PET-MRI apparatus according to a fifth embodiment.

FIG. 11 is a diagram illustrating an exemplary configuration of a PET-MRI apparatus according to the fifth embodiment. For example, as illustrated in FIG. 11, a PET-MRI apparatus 500 according to the fifth embodiment includes the static magnetic field magnet 1, the couch 2, the gradient coil 3, the gradient coil driving circuitry 4, a transmitting radio frequency coil 505*a*, a receiving radio frequency coil 505*b*, the transmitting circuitry 207, the receiving circuitry 208, the plurality of PET detectors 9, the radio frequency shield 10, the console 11, the display 12, the MR data acquiring circuitry 13, the PET data acquiring circuitry 14, the sequence controlling circuitry 15, and the computer 15.

The transmitting radio frequency coil 505*a* is a whole body coil formed to have a hollow and substantially circular cylindrical shape and is installed on the inner circumferential side of the gradient coil 3. Further, when an imaging data acquisition process is performed on the subject S, the transmitting radio frequency coil 505*a* is configured to irradiate a radio frequency magnetic field to the subject S placed in the imaging area, on the basis of the radio frequency pulse output from the transmitting circuitry 307.

The receiving radio frequency coil 505*b* is a local coil formed to have a hollow and substantially circular cylindrical shape and is provided on the couchtop 2*a* of the couch 2. Further, when an imaging data acquisition process is performed on the subject S, the receiving radio frequency coil 505*b* is moved into the imaging area together with the couchtop 2*a* and is configured to detect a magnetic resonance signal emitted from the subject S as a result of the irradiation of the radio frequency magnetic field and to output the detected magnetic resonance signal to the receiving circuitry 208.

For example, the receiving radio frequency coil 505*b* may be a coil for the head, a coil for the neck, a coil for a shoulder, a coil for the chest, a coil for the abdomen, a coil for a leg, a coil for the spine, or the like. FIG. 11 illustrates an example in which the receiving radio frequency coil 505*b* is a coil for the abdomen.

With the configuration described above, in the fifth embodiment, the receiving radio frequency coil 505*b* is a birdcage-type radio frequency coil arranged to enclose therein the subject S and includes two end rings and a plurality of rungs arranged at intervals along the circumferential direction of the end rings. Further, each of the rungs of the receiving radio frequency coil 505*b* is configured to include at least one PET detector 9 and the radio frequency shield that covers the periphery of said at least one PET detector 9.

In this situation, the receiving radio frequency coil 505*b* according to the fifth embodiment has a similar configuration to that of the transmitting and receiving radio frequency coil 5 explained in the first embodiment except for the configuration for the transmission, although the size of the entirety thereof is smaller. Consequently, by using the receiving radio frequency coil 505*b* according to the fifth embodiment, it is possible to inhibit the interference of the PET detectors 9 with the receiving radio frequency coil 505*b*, similarly to the first embodiment.

Figure 12:
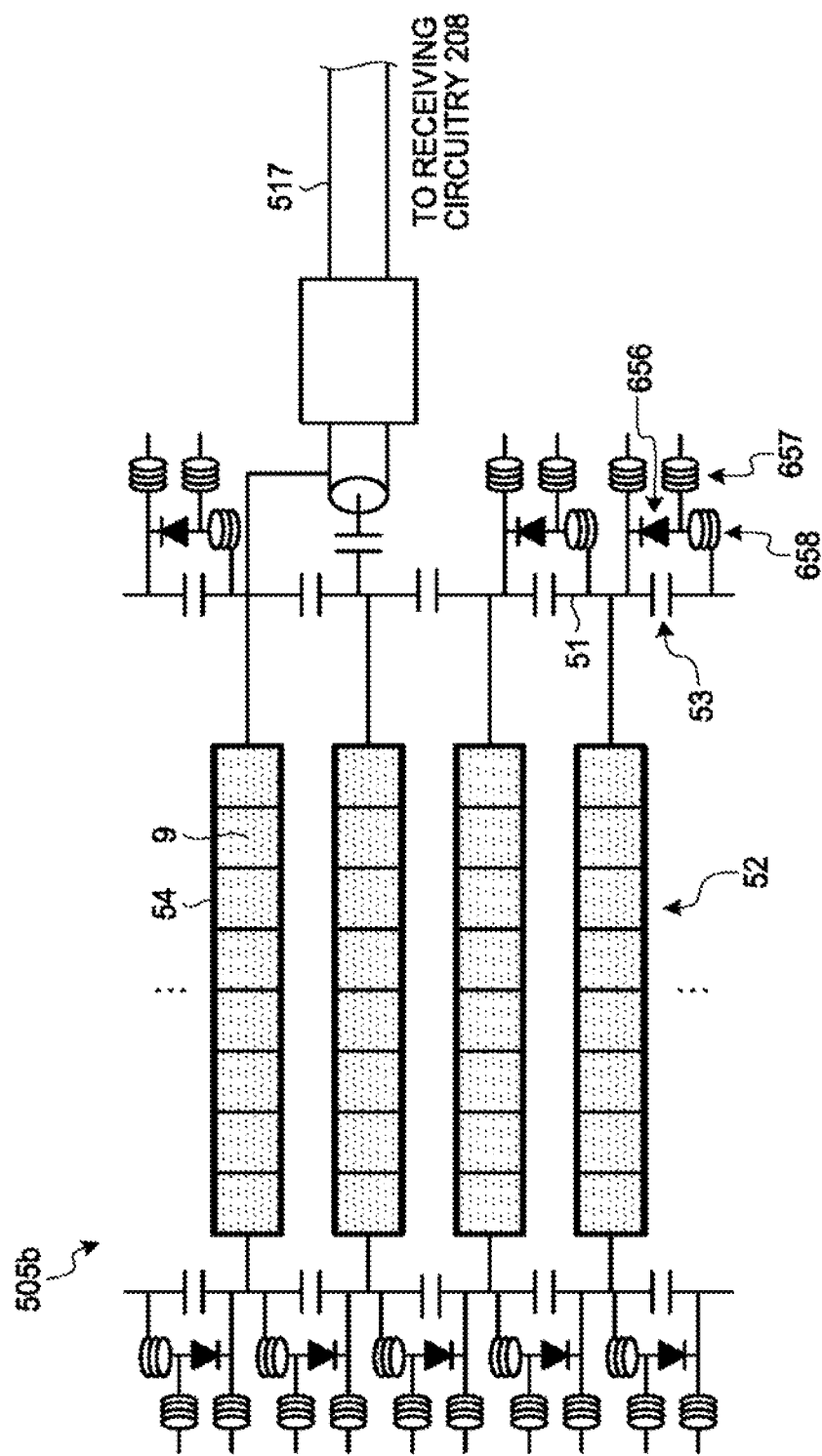
FIG. 12 is a drawing illustrating an example of an electrical connection of a receiving radio frequency coil according to the fifth embodiment.

FIG. 12 is a drawing illustrating an example of an electrical connection of the receiving radio frequency coil 505*b* according to the fifth embodiment. For example, as illustrated in FIG. 12, the PET-MRI apparatus 500 according to the fifth embodiment includes, as units being connected to the receiving radio frequency coil 505*b*, a receiving cable 517 extending to the receiving circuitry 208 and a radio frequency blocking circuitry 18 connected to the receiving cable 517.

Further, the receiving radio frequency coil 505*b* further has a switching function that, for each of the rungs 52, brings the receiving radio frequency coil 505*b* into a desired tuned state at the time of reception and brings the receiving radio frequency coil 505*b* into an untuned state at the time of transmission.

For example, the receiving radio frequency coil 505*b* has, as the switching function, PIN diodes 656 each of which is connected in parallel to a different one of the capacitors 53 in the end rings; two choice power supply cables 657 that are connected to the two ends of each of the PIN diodes 656 and are configured to supply electric power to the PIN diodes 656; and inductors 658. In this situation, the capacitors 53 and the inductors 658 are each regulated so as to resonate at the same frequency as that of the receiving radio frequency coil 505*b*.

At the time of transmission, the PIN diodes 656 are turned on as a result of an electric current flowing in the normal direction of the PIN diodes 656. As a result, the capacitors 53 and the inductors 658 go into a tuned state. Accordingly, the two ends of each of the capacitors 53 have high impedance levels, and the receiving radio frequency coil 505*b* goes into an untuned state. In contrast, at the time of reception, the PIN diodes 656 are turned off as a result of a reverse voltage being applied to the PIN diodes 656 through the choke power supply cables 657. As a result, the receiving radio frequency coil 505*b* goes into a tuned state, so that the receiving radio frequency coil 505*b* is able to receive the magnetic resonance signal.

As explained above, according to the fifth embodiment, similarly to the first embodiment, it is possible to inhibit the interference of the PET detectors 9 with the receiving radio frequency coil 505*b*. It is therefore possible to reduce image quality deterioration that may be caused in the MR image by the PET detectors 9.

Sixth Embodiment

Next, a sixth embodiment will be explained. The sixth embodiment corresponds to an example in which a radio frequency coil including the PET detectors 9 is a local coil formed in accordance with a localized region of interest of the subject S and is configured to receive a magnetic resonance signal emitted from the subject S. Further, the sixth embodiment corresponds to the example in which the radio frequency coil is moved by a drivable table that is different from the couch 2.

Figure 13:
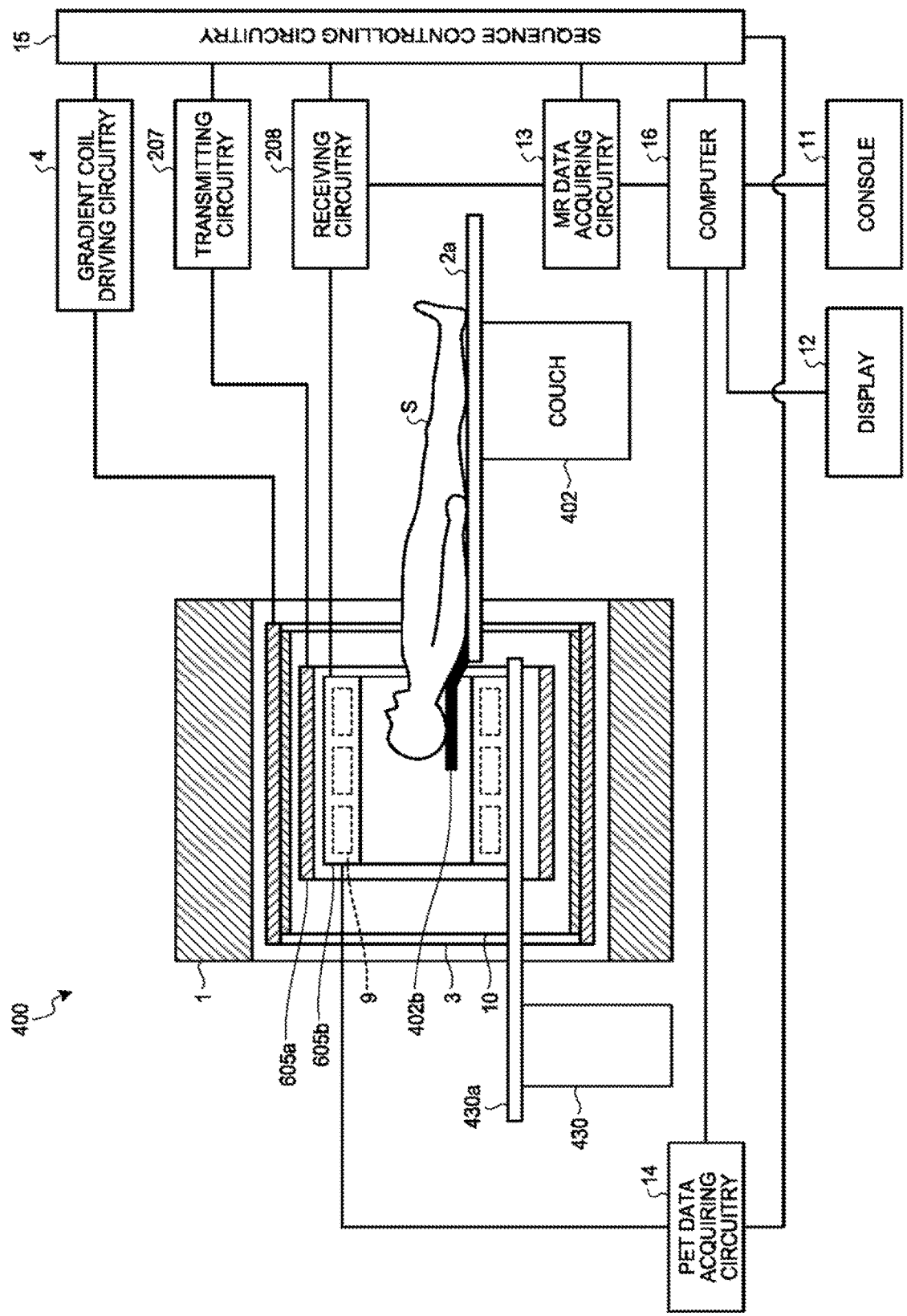
FIG. 13 is a diagram illustrating an exemplary configuration of a PET-MRI apparatus according to a sixth embodiment.

FIG. 13 is a diagram illustrating an exemplary configuration of a PET-MRI apparatus according to the sixth embodiment. For example, as illustrated in FIG. 13, a PET-MRI apparatus 400 according to the sixth embodiment includes the static magnetic field magnet 1, the couch 402, the gradient coil 3, the gradient coil driving circuitry 4, a transmitting radio frequency coil 303*a*, a receiving radio frequency coil 605*b*, the transmitting circuitry 207, the receiving circuitry 208, the plurality of PET detectors 9, the radio frequency shield 10, the console 11, the display 12, the MR data acquiring circuitry 13, the PET data acquiring circuitry 14, the sequence controlling circuitry 15, the computer 16, and the radio frequency coil insertion table 430.

The transmitting radio frequency coil 505*a* is a whole body coil formed to have a hollow and substantially circular cylindrical shape and is installed on the inner circumferential side of the gradient coil 3. Further, when an imaging data acquisition process is performed on the subject S, the transmitting radio frequency coil 605a is configured to irradiate a radio frequency magnetic field to the subject S placed in the imaging area, on the basis of the radio frequency pulse output from the transmitting circuitry 207.

The receiving radio frequency coil 605b is a local coil formed to have a hollow and substantially circular cylindrical shape and is provided on the insertion plate 430a of the radio frequency coil insertion table 430. Further, when an imaging data acquisition process is performed on the subject S, the receiving radio frequency coil 605b is moved into the imaging area together with the insertion plate 430a and is configured to detect a magnetic resonance signal emitted from the subject S as a result of the irradiation of the radio frequency magnetic field and to output the detected magnetic resonance signal to the receiving circuitry 208.

For example, the receiving radio frequency coil 605b may be a coil for the head, a coil for the neck, a coil for a leg, or the like. FIG. 13 illustrates an example in which the receiving radio frequency coil 605b is a coil for the head.

With the configuration described above, in the sixth embodiment, the receiving radio frequency coil 605b is a birdcage-type radio frequency coil arranged to enclose therein the subject S and includes two end rings and a plurality of rungs arranged at intervals along the circumferential direction of the end rings. Further, each of the rungs of the receiving radio frequency coil 605b is configured to include at least one PET detector 9 and the radio frequency shield that covers the periphery of said at least one PET detector 9.

In this situation, the receiving radio frequency coil 605b according to the sixth embodiment has a similar configuration to that of the transmitting and receiving radio frequency coil 5 explained in the first embodiment except for the configuration for the transmission, although the size of the entirety thereof is smaller. Consequently, by using the receiving radio frequency coil 605b according to the sixth embodiment, it is possible to inhibit the interference of the PET detectors 9 with the receiving radio frequency coil 605b, similarly to the first embodiment. In this situation, the receiving radio frequency coil 605b according to the sixth embodiment also includes the same configuration as the switching function illustrated in FIG. 12.

As explained above, according to the sixth embodiment, similarly to the first embodiment, it is possible to inhibit the interference of the PET detectors 9 with the receiving radio frequency coil 605b. It is therefore possible to reduce image quality deterioration that may be caused in the MR image by the PET detectors 9.

The radio frequency coils including the PET detectors 9 explained in the third to the sixth embodiments above are each a local coil, provided on the outside of the gantry housing therein the static magnetic field magnet 1 and the gradient coil 3. Accordingly, any of the radio frequency coils according to the third to the sixth embodiments may be used as being connected to an MRI apparatus that has no functions of a PET apparatus. In that situation, the local coil including the PET detectors S and the PET data acquiring circuitry 14 are each employed as being additionally connected to the MRI apparatus having no functions of a PET apparatus. By using configuration, it is possible to realize a PET-MRI apparatus at a lower cost than the situation where a PET-MRI apparatus is realized, to begin with, so as to have the functions of both an MRI apparatus and a PET apparatus.

The first to the sixth embodiments have thus been explained. It is also possible to carry out any of the embodiments described above by further modifying the configurations thereof. In the following sections, a number of modification examples that can similarly be applied to any of the embodiments will be explained.

First Modification Example

To start with, a first modification example will be explained. The first modification example corresponds to a situation in which a radio frequency shield covering the PET detectors 9 has formed therein slits for the purpose of reducing an eddy current.

Figure 14:
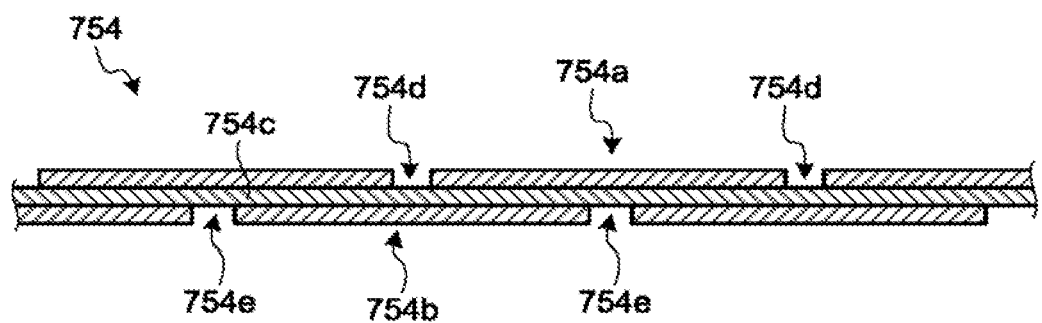
FIG. 14 is a drawing illustrating an exemplary configuration of a radio frequency shield according to a first modification example.

FIG. 14 is a drawing illustrating an exemplary configuration of the radio frequency shield according to the first modification example. FIG. 14 provides a cross-sectional view of a radio frequency shield 754 covering the PET detectors S. For example, as illustrated in FIG. 14, in the first modification example, the radio frequency shield 754 includes a first conductor 754a, a second conductor 754b, and a dielectric member 754c, each having a plate-like shape. In this situation, the first conductor 754a is arranged on a first surface of the dielectric member 754c, whereas the second conductor 754b is arranged on a second surface of the dielectric member 754c.

Further, the first conductor 754a has formed therein a plurality of linear-shaped slits 754d at predetermined intervals. The second conductor 754b also has formed therein a plurality of linear-shaped slits 754e at the same intervals. In this situation, the first conductor 754a and the second conductor 754b are arranged in such a manner that the slits formed in the two conductors extend parallel to one another, while the positions of the slits formed in the two conductors are staggered in a direction orthogonal to the slits. In this situation, the slits formed in the first conductor 754a and the second conductor 754b may be formed along the axial direction of the radio frequency coil or may be formed along the circumferential direction thereof.

In this configuration, because the first conductor 754a and the second conductor 754b arranged on the two surfaces of the dielectric member 754c have the slits formed therein, the part interposed between the first conductor 754a and the second conductor 754b forms a capacitor (a capacitive element). In this situation, by arranging the thickness of the dielectric member 754c to be sufficiently small, it is possible to keep the impedance of the capacitor sufficiently low with respect to the magnetic resonance frequency. As a result, the radio frequency shield 754 is considered as a sufficiently good conductor at the magnetic resonance frequency and is thus able to function as a radio frequency shield.

As explained above, in the first modification example, because the radio frequency shield 754 covering the PET detector 9 has the slits formed therein, it is possible to reduce the eddy current induced on the surfaces of the radio frequency shield 754 by the gradient magnetic field. As a result, it is possible to prevent image quality deterioration that may be caused in the MR image or the PET image by an eddy-current magnetic field generated by the eddy current.

Second Modification Example

Next, a second modification example will be explained. The second modification example corresponds to a situation in which a radio frequency shield covering the PET detectors 9 is formed by using a net-like member.

Figure 15:
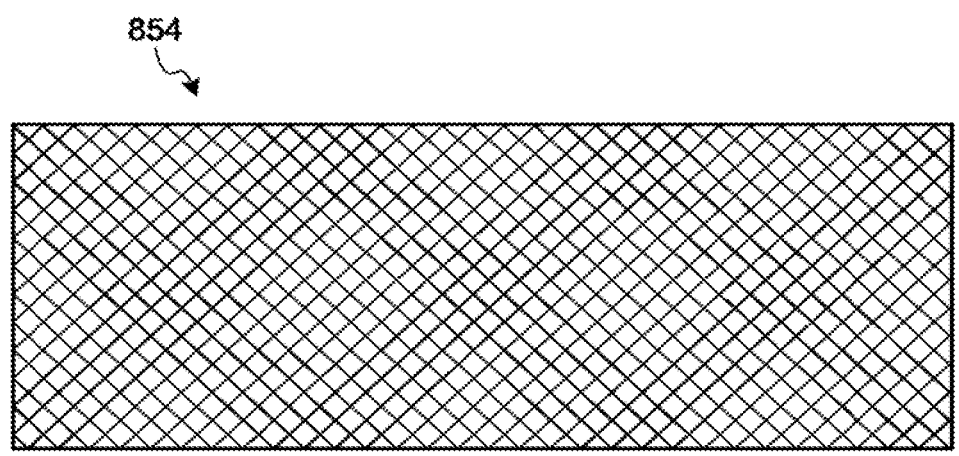
FIG. 15 is a drawing illustrating an exemplary configuration of a radio frequency shield according to a second modification example.

FIG. 15 is a drawing illustrating an exemplary configuration of the radio frequency shield according to the second modification example. FIG. 15 illustrates an exterior appearance of a radio frequency shield 854 covering the PET detectors 9. For example, as illustrated in FIG. 15, in the second modification example, the radio frequency shield 854 is formed by using a member being made of metal and having a net structure.

As explained above, in the second modification example, because the radio frequency shield 854 covering the PET detectors 9 is formed by using the net-like member, the cross-sectional area of the conductor in the radio frequency shield 854 is smaller, which makes it more difficult for the eddy current generated by the gradient to flow. In addition, because the surface area of the net wires exerts an effect in relation to the radio frequency waves, it is possible to ensure a sufficiently large surface area by arranging the mesh of the net to be fine to a certain extent and to enable the net-like member to function as a radio frequency shield.

Third Modification Example

Next, a third modification example will be explained. The third modification example corresponds to a situation where the rungs of a radio frequency coil including the PET detectors 9 are positioned at an angle with respect to the circumferential direction of the end rings, along the surface of the circular cylinder of the radio frequency coil.

Figure 16:
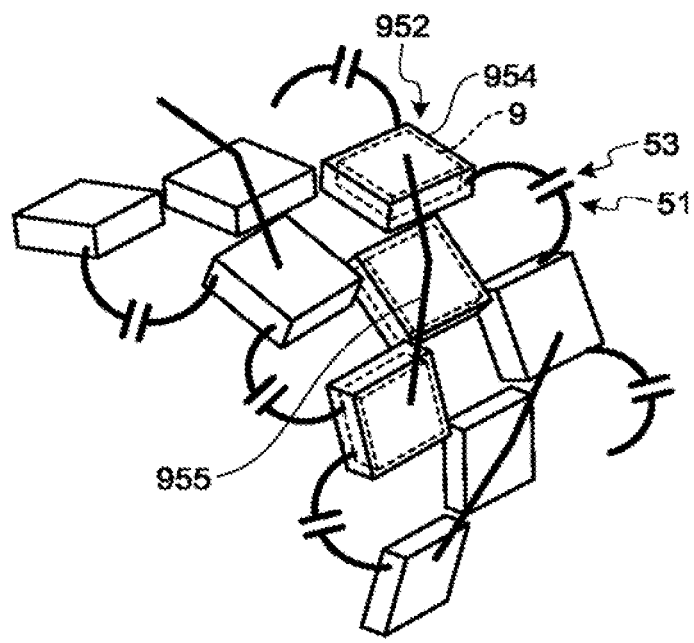
FIG. 16 is a drawing illustrating an exemplary configuration of a radio frequency coil according to a third modification example.
Figure 17:
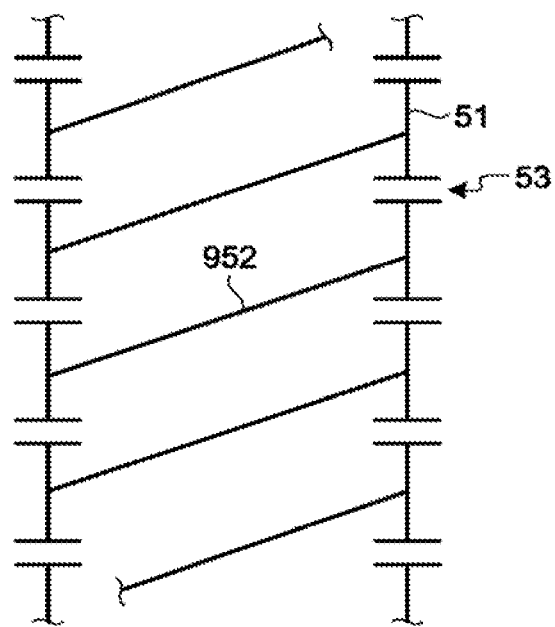
FIG. 17 is a diagram illustrating an exemplary configuration of the radio frequency coil according to the third modification example.

FIGS. 16 and 17 are a drawing and a diagram illustrating exemplary configurations of the radio frequency coil according to the third modification example. The examples in FIGS. 16 and 17 illustrate only a number of rungs among the rungs included in the radio frequency coil, for the sake of convenience in illustration. Further, FIG. 17 illustrates an electrical circuit equivalent to that of the radio frequency coil.

For example, as illustrated in FIG. 16, in the third modification example, each of rungs 952 of the radio frequency coil, includes two or more PET detectors 9 that are arranged in a direction diagonal to the circumferential direction of the end rings 51, along the surface of the circular cylinder of the radio frequency coil. Further, a separate radio frequency shield 954 individually covers the periphery of each of the plurality of PET detectors 9, while the radio frequency shields 954 are electrically connected to one another by conductor pieces 955, for example.

In other words, in the third modification example, a plurality of PET detectors 9 are arranged along the circumferential direction of the radio frequency coil, while a plurality of rows in which the PET detectors 9 are arranged in the circumferential direction are arranged along the axial direction of the radio frequency coil, in such a manner that the positions thereof are staggered in the circumferential direction of the radio frequency coil.

Further, for example, as illustrated in FIG. 17, in the third modification example, the rungs 952 are formed by connecting together, while using the conductor pieces 955, the radio frequency shields 954 that are positioned next to each other in the direction diagonal to the circumferential direction of the end rings 51. Further, each of the end rings 51 is structured by connecting together the radio frequency shields 954 covering the PET detectors 9 and being positioned at either one of the two ends of the plurality of rungs 952, while interposing the capacitor 55 between any two radio frequency shields 954 that are adjacently positioned in the circumferential direction.

In the description above, the example is explained in which the rungs 952 are structured by the PET detectors 9 positioned next to each other in the diagonal direction; however, possible embodiments are not limited to this example. For instance, while the PET detectors 9 are arranged in the same manner as described above, rungs may be structured by the PET detectors 9 positioned next to each other in the axial direction. In that situation, the quantity of PET detectors 9 contained in each rung varies among the rungs. In that situation, the impedance may vary among the rungs 952. In contrast, when the rungs 952 are structured by the PET detectors 9 positioned next to each other in the diagonal direction as illustrated in FIG. 16. It is possible to prevent the impedance levels from varying among the rungs, unlike the situation described above.

Further, although FIG. 16 illustrates the example in which the separate radio frequency shield is individually provided for each of the PET detectors 9, one radio frequency shield may be provided for the two or more PET detectors 9 arranged along the axial direction.

As explained above, according to the third modification example, the rungs 952 of the radio frequency coil are positioned at an angle with respect to the circumferential direction of the end rings 51, along the surface of the circular cylinder of the radio frequency cool. In this configuration, because the plurality of PET detectors 9 are arranged so as to be staggered in the circumferential direction of the radio frequency coil, it is possible to detect the gamma rays in a more spatially-uniform manner.

Fourth Modification Example

Next, a fourth modification example will be explained. The fourth modification example corresponds to a situation in which one or more rungs non-exhaustively selected from among the plurality of rungs included in a radio frequency coil including the PET detectors 9 each have, in at least a portion thereof, a gap formed so as to penetrate from the inner circumferential side to the outer circumferential side of the radio frequency coil.

Figure 18:
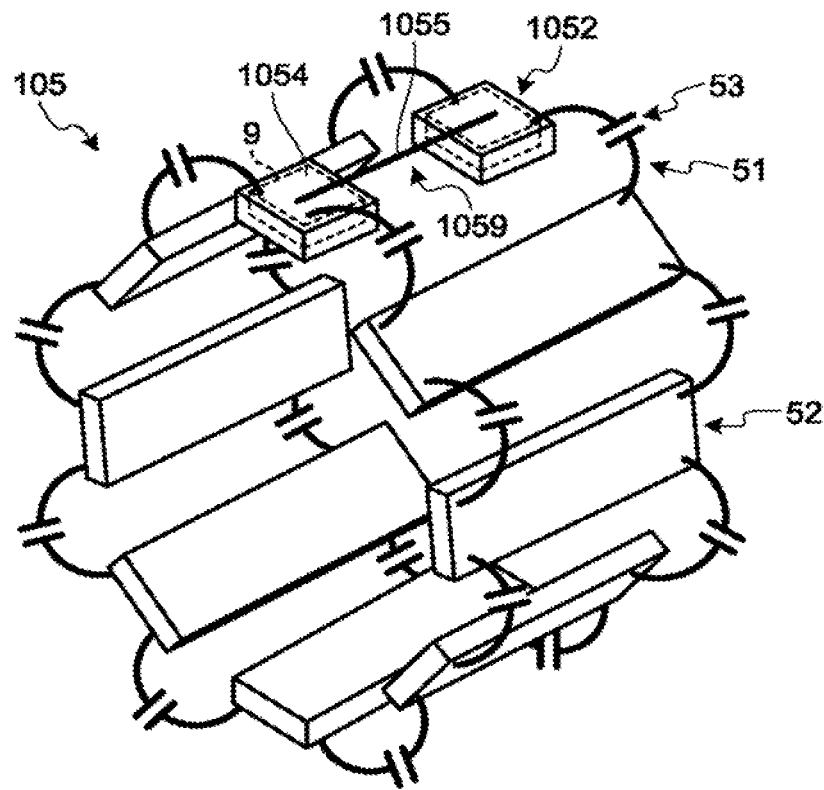
FIG. 18 is a drawing illustrating an exemplary configuration of a radio frequency coil according to a fourth modification example.
Figure 19:
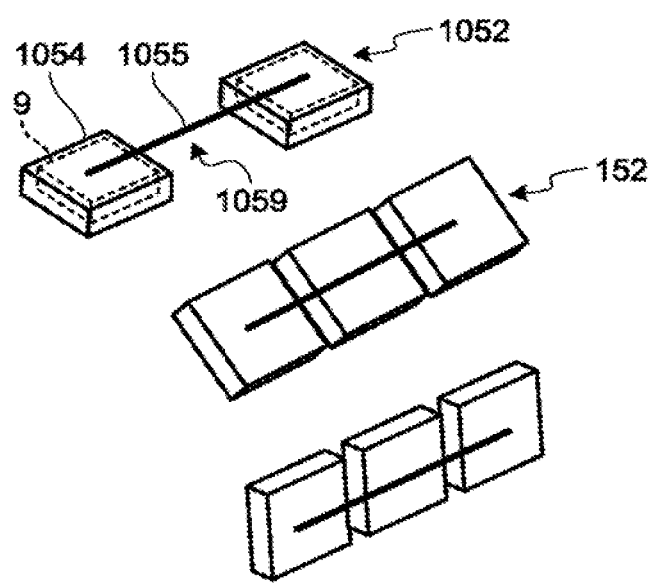
FIG. 19 is a drawing illustrating an exemplary configuration of another radio frequency coil according to the fourth modification example.

FIGS. 18 and 19 are drawings illustrating exemplary configurations of radio frequency coils according to the fourth modification example. FIG. 18 illustrates an example obtained by modifying the radio frequency coil illustrated in FIG. 2. FIG. 19 illustrates an example obtained by modifying the radio frequency coil illustrated in FIG. 3.

For example, as illustrated in FIG. 18, in the fourth modification example, at least one rung 1052 non-exhaustively selected from among the plurality of rungs included in a radio frequency coil 105 has a gap 1059 formed to penetrate from the inner circumferential side to the outer circumferential side of the radio frequency coil 105.

For example, said at least one rung 1052 includes two or more PET detectors 9 arranged along the axial direction of the radio frequency coil 105. In this situation, the two or more PET detectors 9 included in said at least one rung 1052 are arranged in areas excluding the vicinity of the center in terms of the axial direction of the radio frequency coil 105. Further, with respect to the two or more PET detectors 9, one or more separate radio frequency shields 1054 each individually cover the periphery of one PET detector 9 or multiple PET detectors 9, while the radio frequency shields 1054 are electrically connected to one another by conductor pieces 1055, for example.

In this configuration, the rung 1052 is provided with the gap 1059 formed in the vicinity of the center in terms of the axial direction of the radio frequency coil 105. In this situation, for example, the size of the gap 1059 is determined in accordance with the purpose of the radio frequency coil 105. In that situation, the gamma rays emitted to the position of the gap 1059 are complemented, for example, by a data interpolation process performed by the PET image generating function of the computer 16.

The rungs other than said at least, one rung 1052 each have the same configuration as that of each of the rungs 52 illustrated in FIG. 2. Alternatively, as illustrated in FIG. 19 for example, the rungs other than said at least one rung 1052 may have the same configuration as that of each of the rungs 152 illustrated in FIG. 3.

As explained above, in the fourth modification example, at least one rung 1052 non-exhaustively selected from among the plurality of rungs included in the radio frequency coil 105 is provided with the gap 1059 formed in at least a portion thereof. For example, the radio frequency coil 105 according to the fourth modification example is used as a radio frequency coil for the head and is to be attached so that the gap 1053 is positioned in front of the eyes of the subject. This arrangement makes it possible to take an MR image or a PET image without blocking the field of vision of the subject.

According to at least one aspect of the embodiments described above, it is possible to reduce image quality deterioration that may be caused in an MR image by the PET detectors, in the PET-MRI apparatus.

While certain embodiments have been described, these embodiments have been presented by way of example only, and are not intended to limit the scope of the inventions. Indeed, the novel embodiments described herein say be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A PET-MRI apparatus comprising:
    a static magnetic field magnet configured to generate a static magnetic field;
    a gradient coil configured to apply a gradient magnetic field to a subject placed in the static magnetic field;
    a birdcage-type radio frequency coil that includes two end rings and a plurality of rungs arranged at intervals along a circumferential direction of the end rings and that is configured to transmit a radio frequency pulse or to receive a magnetic resonance signal from the subject; and
    at least one PET detector configured to detect gamma rays emitted from the subject, wherein
    the at least one PET detector is encased in at least one rung of the plurality of rungs of the radio frequency coil, wherein the at least one rung of the plurality of rungs comprises a conductor.

2. The PET-MRI apparatus according to claim 1, wherein the radio frequency coil is a local coil provided on an outside of a gantry housing therein the static magnetic field magnet and the gradient coil.

3. The PET-MRI apparatus according to claim 1, wherein the conductor of at least one rung of the plurality of rungs covers a periphery of the PET detector and is configured to function as a radio frequency shield.

4. The PET-MRI apparatus according to claim 1, wherein the radio frequency coil is a whole body coil installed on an inside of the static magnetic field magnet and the gradient coil.

5. The PET-MRI apparatus according to claim 1, wherein
    the rungs include a plurality of PET detectors, and
    an integrally-formed radio frequency shield covers a periphery of the PET detectors.

6. The PET-MM apparatus according to claim 1, wherein
    the rungs include a plurality of PET detectors,
    one or snore separate radio frequency shields each individually cover a periphery of a different one of the plurality of PET detectors or two or more of the plurality of PET detectors, and
    the radio frequency shields are electrically connected to one another.

7. The PET-MM apparatus according to claim 1, wherein the rungs are positioned at an angle with respect to the circumferential direction of the end rings, along a surface of a circular cylinder of the radio-frequency coil.

8. The PET-MM apparatus according to claim 1, wherein the PET detector includes:
    a signal detector configured to detect the gave a rays by converting the gamma rays into an analog signal;
    an amplifier configured to amplify the analog signal output from the signal detector; and
    a converter configured to convert the analog signal amplified by the amplifier into a digital signal.

9. The PET-MRI apparatus according to claim 1, wherein the conductor of at least one rung of the plurality of rungs has a slit formed therein.

10. The PET-MRI apparatus according to claim 1, wherein at least one of a signal line and a control line connected to the PET detector is provided so as to extend on an equipotential surface of the radio frequency coil.

11. The PET-MRI apparatus according to claim 1, wherein at least one of a signal line and a control line connected to the PET detector is covered by a radio frequency shield.

12. The PET-MRI apparatus according to claim 1, wherein one or more rungs of the plurality of rungs each have, in at least a portion thereof, a gap formed so as to penetrate from an inner circumferential side to an outer circumferential side of the radio frequency coil.

13. A radio frequency coil, comprising
    two end rings; and
    a plurality of rungs arranged at intervals along a circumferential direction of the end rings and configured to transmit a radio frequency pulse or to receive a magnetic resonance signal from a subject at least one PET detector configured to detect gamma rays emitted from the subject is encased in at least one rung of the plurality of runs of the radio frequency coil, wherein the at least one rung of the plurality of rungs comprises a conductor.

* * * * *